(12) United States Patent
Greenstein et al.

(10) Patent No.: US 9,877,644 B2
(45) Date of Patent: Jan. 30, 2018

(54) OPTICAL SPECULUM

(71) Applicant: Illumigyn Ltd., Neve Ilan (IL)

(72) Inventors: Lior Greenstein, Tel Aviv (IL); Gilad A. Davara, Rehovot (IL); Gad Ganon, Yad Hana (IL); David Aviv, Hadera (IL)

(73) Assignee: Illumigyn Ltd., Neve Ilan (IL)

( * ) Notice: Subject to any disclaimer, the term of this patent is extended or adjusted under 35 U.S.C. 154(b) by 0 days.

(21) Appl. No.: 15/056,361

(22) Filed: Feb. 29, 2016

(65) Prior Publication Data

US 2016/0262604 A1 Sep. 15, 2016

Related U.S. Application Data

(63) Continuation-in-part of application No. 14/030,083, filed on Sep. 18, 2013, now Pat. No. 9,271,640, which
(Continued)

(51) Int. Cl.
*A61B 1/32* (2006.01)
*A61B 1/04* (2006.01)
(Continued)

(52) U.S. Cl.
CPC .......... *A61B 1/32* (2013.01); *A61B 1/00006* (2013.01); *A61B 1/00009* (2013.01);
(Continued)

(58) Field of Classification Search
CPC ... A61B 1/32; A61B 1/00006; A61B 1/00009; A61B 1/00103; A61B 1/00105;
(Continued)

(56) References Cited

U.S. PATENT DOCUMENTS 4,210,133 A * 7/1980 Castaneda .............. A61B 1/303
600/102
4,491,131 A 1/1985 Vassiliadis
(Continued)

FOREIGN PATENT DOCUMENTS

WO 8925512 A1 6/1998

OTHER PUBLICATIONS

International Search Report and Written Opinion for Application No. PCT/IB14/64638, dated Feb. 4, 2015, 12 pages.
(Continued)

*Primary Examiner* — Pedro Philogene
*Assistant Examiner* — David C Comstock
(74) *Attorney, Agent, or Firm* — Brooks Kushman P.C.

(57) ABSTRACT

A system for direct imaging and diagnosing of abnormal cells in a target tissue includes an image acquisition system comprising a plurality of independently movable optical elements. The image acquisition system is arranged to capture at least one of a single image or multiple images or video of cells within the target tissue using at least one of bright field or dark field source divided into independently operated segments to obtain a plurality of data sets. An image analysis and control unit in communication with the image acquisition system analyzes the data sets and applies algorithms to the data sets for diagnosing abnormal cells.

12 Claims, 19 Drawing Sheets

Related U.S. Application Data is a continuation-in-part of application No. 12/943,170, filed on Nov. 10, 2010, now Pat. No. 8,638,995.

(60) Provisional application No. 61/259,663, filed on Nov. 10, 2009.

(51) Int. Cl.
| | | |
|---|---|---|
| *A61B 1/303* | (2006.01) | |
| *A61B 1/00* | (2006.01) | |
| *A61B 18/20* | (2006.01) | |
| *A61B 18/22* | (2006.01) | |
| *A61B 18/00* | (2006.01) | |
| *A61B 1/06* | (2006.01) | |

(52) U.S. Cl.
CPC ...... *A61B 1/00103* (2013.01); *A61B 1/00105* (2013.01); *A61B 1/042* (2013.01); *A61B 1/043* (2013.01); *A61B 1/0684* (2013.01); *A61B 1/303* (2013.01); *A61B 18/201* (2013.01); *A61B 18/22* (2013.01); *A61B 1/00059* (2013.01); *A61B 1/00188* (2013.01); *A61B 1/0638* (2013.01); *A61B 2018/00559* (2013.01); *A61B 2018/00577* (2013.01); *A61B 2018/00642* (2013.01); *A61B 2018/00708* (2013.01); *A61B 2018/00904* (2013.01); *A61B 2018/00982* (2013.01); *A61B 2018/2065* (2013.01); *A61B 2018/20359* (2017.05); *A61B 2018/2266* (2013.01); *A61B 2218/007* (2013.01)

(58) Field of Classification Search
CPC ....... A61B 1/042; A61B 1/043; A61B 1/0684; A61B 1/303; A61B 1/00059; A61B 1/00188; A61B 1/0638; A61B 18/201; A61B 18/22; A61B 2018/00559; A61B 2018/00577; A61B 2018/00642; A61B 2018/00708; A61B 2018/00904; A61B 2018/00982; A61B 2018/2065; A61B 2018/2095; A61B 2018/2266; A61B 2218/007
USPC ....... 600/205, 214, 215, 220–223, 104, 167, 600/109
See application file for complete search history.

(56) References Cited

U.S. PATENT DOCUMENTS

| | | |
|---|---|---|
| 4,905,670 A | 3/1990 | Adair |
| 5,143,054 A | 9/1992 | Adair |
| 5,179,938 A | 1/1993 | Lonky |
| 5,251,613 A | 10/1993 | Adair |
| 5,717,844 A | 2/1998 | Lo et al. |
| D395,084 S | 6/1998 | Krauter et al. |
| 5,791,346 A | 8/1998 | Craine et al. |
| 5,836,872 A | 11/1998 | Kenet et al. |
| 5,840,012 A | 11/1998 | Krauter et al. |
| 5,846,249 A | 12/1998 | Thompson |
| D416,088 S | 11/1999 | Krauter et al. |
| 6,068,593 A | 5/2000 | Krauter et al. |
| 6,101,408 A | 8/2000 | Craine et al. |
| 6,106,457 A | 8/2000 | Perkins et al. |
| 6,147,705 A | 11/2000 | Krauter et al. |
| 6,277,067 B1 | 8/2001 | Blair |
| 6,346,085 B1 | 2/2002 | Schiffman |
| 6,359,644 B1 | 3/2002 | Salvati |
| 6,496,718 B1 | 12/2002 | Lonky |
| 6,595,917 B2 | 7/2003 | Nieto |
| 6,712,761 B2 | 3/2004 | Borodulin et al. |
| 6,766,184 B2 | 7/2004 | Utzinger et al. |
| 8,064,976 B2 | 11/2011 | Ince |
| 8,602,971 B2 | 12/2013 | Farr |
| 2003/0138923 A1 | 7/2003 | Palsson |
| 2003/0225313 A1 | 12/2003 | Borodulin et al. |
| 2004/0064053 A1 | 4/2004 | Chang et al. |
| 2004/0186355 A1 | 9/2004 | Strong et al. |
| 2004/0220478 A1 | 11/2004 | Wallace et al. |
| 2005/0234305 A1 | 10/2005 | Licciardi |
| 2006/0122463 A1 | 7/2006 | Klaassen |
| 2006/0276693 A1 | 12/2006 | Pacey |
| 2007/0024846 A1 | 2/2007 | Allweier |
| 2007/0112273 A1 | 5/2007 | Rogers |
| 2007/0135687 A1* | 6/2007 | Balas ............... A61B 1/303 600/221 |
| 2007/0161876 A1 | 7/2007 | Bambot et al. |
| 2007/0270653 A1 | 11/2007 | Vayser et al. |
| 2008/0045799 A1 | 2/2008 | Whitehead et al. |
| 2008/0108869 A1 | 5/2008 | Sanders et al. |
| 2008/0108877 A1* | 5/2008 | Bayat ............... A61B 17/02 600/214 |
| 2008/0208006 A1 | 8/2008 | Farr |
| 2008/0306345 A1 | 12/2008 | Balas |
| 2008/0312508 A1 | 12/2008 | Shulman |
| 2009/0082695 A1 | 3/2009 | Whitehead |
| 2009/0177044 A1 | 7/2009 | Cohen et al. |
| 2009/0205665 A1 | 8/2009 | Tanaka et al. |
| 2009/0216088 A1 | 8/2009 | Danna et al. |
| 2009/0237653 A1 | 9/2009 | Schnitzlein et al. |
| 2009/0312610 A1* | 12/2009 | Buchok ............ A61B 1/00137 600/205 |
| 2009/0326331 A1 | 12/2009 | Rosen |
| 2010/0149315 A1 | 6/2010 | Qu et al. |
| 2011/0112408 A1 | 5/2011 | Greenstein et al. |
| 2012/0078060 A1* | 3/2012 | Swift ............... A61B 1/32 600/220 |
| 2012/0150164 A1 | 6/2012 | Lee et al. |
| 2012/0218514 A1 | 8/2012 | Kwong |

OTHER PUBLICATIONS

Extended European Search Report for Application No. 14845457.2, dated Apr. 13, 2017, 10 pages.

\* cited by examiner

OPTICAL SPECULUM

CROSS-REFERENCE TO RELATED APPLICATIONS

This application is a continuation-in-part of U.S. patent application Ser. No. 14/030,083 filed Sep. 18, 2013, which is a continuation-in-part of U.S. patent application Ser. No. 12/943,170 filed Nov. 10, 2010, now U.S. Pat. No. 8,638,995 which, in turn, claims the benefit of U.S. provisional Application No. 61/259,663, filed Nov. 10, 2009, the disclosures of which are hereby incorporated in their entirety by reference herein.

TECHNICAL FIELD

This invention relates in general to an optical system, such as for use as a speculum in colposcopy, gynecology examination hysteroscopy, and detecting and/or removing abnormal cells. In particular, it relates to an optical speculum comprising an improved image acquisition system in which the various optical elements can be moved independently of one another.

BACKGROUND

Uterine cervical cancer is the second most common cancer in women worldwide, with nearly 500,000 new cases and over 270,000 deaths annually. Colposcopy is a medical diagnostic method that is used to detect cervical intraepithelial neoplasia (CIN) and cancer, together with a cytological screen (Papanicolaou smear; i.e., Pap smear). Colposcopy is a medical diagnostic procedure for viewing the cervix and the tissues of the vagina and vulva, and is a common gynecology procedure following an abnormal Pap smear. A colposcope is a low powered binocular microscope with a light source, magnifying lens, and imaging sensor for viewing and inspection of internal cavities, and may include video.

Colposcopy is the leading diagnostic method that is used to detect Cervical Intraepithelial Neoplasia (CIN) and cancer, together with cytological screen (Papanicolaou smear—Pap smear). The purpose of a colposcopic examination is to identify and rank the severity of lesions, so that biopsies representing the highest-grade abnormality can be taken, if necessary. A green filter or green light source such as an LED may be used to accentuate vasculature. During the examination, a 3-5% acetic acid solution is applied to the cervix, causing abnormal and metaplastic epithelia to turn white. Cervical cancer precursor lesions and invasive cancer exhibit certain distinctly abnormal morphologic features that can be identified by colposcopy examination.

Cervical cancer precursor lesions and invasive cancer exhibit certain distinctly abnormal morphologic features that can be identified by colposcopic examination. The purpose of this examination is to identify and rank the severity of lesions, so that biopsies representing the highest grade abnormality can be taken, if necessary. During the examination, a 3-5% acetic acid solution is applied to the cervix, causing abnormal and metaplastic epithelia to turn white. A green filter or green light source such as an LED may be used to accentuate vasculature.

Today, the standard procedure for a gynecological exam invoices the use of a standard speculum with which the physician does a visual examination of the interior vaginal cavity, without any control of optimal illumination or proper optical magnification, thus creating the possibility of missing the detection of abnormal cells.

The optical system is frequently introduced via a speculum that also serves to dilate the body cavity. In order to maximize the likelihood of the success of the procedure, the speculum and the optical system, must meet several important design criteria. In particular, the optical system must be kept clear of opaque material such as bodily fluids so that the surgeon can have an unobstructed view of the tissue of interest. In addition, the optical system must be kept centered with respect to the longitudinal axis of the speculum and with respect to the body cavity being viewed (e.g. the cervix in the case of a vaginal speculum).

Low cost and high-resolution colposcopy could have a direct impact on improving women's health care, reducing examination costs and avoidance of embarrassment. A low-cost hand-held image acquisition device would also assist the gynecologist in every day procedures and or the expert colposcopist, and improve screening cost-effectiveness in developing countries. Thus, a low-cost system comprising a speculum and an optical system appropriate for high-resolution colposcopy remains a long-felt but as yet unmet need.

SUMMARY

It is therefore an object of the present invention to disclose a system for direct imaging diagnosing and (optionally) removing abnormal cells in a target tissue, comprising: an image acquisition system comprising a plurality of optical elements arranged to capture at least one of a single image or multiple images or video of cells within the target tissue using at least one of bright field or dark field source divided into independently operated segments to obtain a plurality of data sets, said optical elements slidably mounted to a track and in mechanical connection with a sliding mechanism that provides independent motion to each of said optical elements; and an image analysis and control unit in communication with the image acquisition system, the image analysis and control unit analyzing the data sets and applying algorithms to the data sets for diagnosing abnormal cells. In some preferred embodiments, the sliding mechanism comprises at least one motor.

It is a further object of the present invention to disclose the system as defined in any of the above; wherein the image acquisition system integrates Bright field illumination, Dark Field illumination, UV light, IR light, RGB light, white light and any combination thereof.

It is a further object of the present invention to disclose the system as defined in any of the above, wherein the image acquisition system has three separate and independent illuminations: White/Monochromatic/IR and UV fluorescence Bright Field (BF) Illumination, White/Monochromatic Dark Field (DF) illumination for diffusive illumination and divided into segments for independent operation, UV LED located behind a dichroic mirror for Fluorescence, and Bright Field (BF) multi spectral illumination.

It is a further object of the present invention to disclose the system as defined in any of the above, wherein the image analysis is integrated and performed within said image acquisition system, located externally to said image acquisition system and any combination thereof.

It is a further object of the present invention to disclose the system as defined in any of the above, comprising a laparoscope, wherein said system is assembled on and mechanically secured to said laparoscope and hysteroscope. In some embodiments, the system further comprises a locking mechanism between the laparoscope and the image acquisition system to assure image acquisition without distortions. In some embodiments, said laparoscope integrates a light collimation element guide for dark field illumination with an optical window.

It is a further object of the present invention to disclose the system as defined in any of the above, wherein the image acquisition system includes one or more high resolution imaging sensors; one of which is adapted to capture one or more images in definitive spectrum; and, the second one is adapted to capture one or more images for visualizing for the physician's live view.

It is a further object of the present invention to disclose the system as defined in any of the above, wherein the images are transmitted to separate channels of said image analysis and control unit and presented separately on a screen.

It is a further object of the present invention to disclose the system as defined in any of the above, wherein the image acquisition system further comprises a laser ablation module with a 2-D moveable mirror system to enable accurate ablation of abnormal cells, wherein said laser ablation module uses said data sets to eliminate the diagnosed abnormal cells, and the image acquisition system is designed to stop ablation when it is detected that abnormal cells no longer exist in the image. In some embodiments, the laser ablation module comprises a pulsed laser beam selected from the group consisting of infrared laser beam, green laser beam, and ultraviolet laser beam, said laser beam guided via a high power fiber to said target tissue using an imaging lens for focusing said pulse beam with sufficient pulse energy and pulse peak power to remove abnormal cells.

It is a further object of the present invention to disclose the system as defined in any of the above, wherein said system is an optical disposable speculum.

It is a further object of the present invention to disclose the system as defined in any of the above, wherein the optical disposable speculum comprises an optical window provided with a layer of elastic material disposed so as to prevent stray light from entering said image acquisition system.

It is a further object of the present invention to disclose the system as defined in any of the above, wherein the optical disposable speculum is a single-use speculum.

It is a further object of the present invention to disclose the system as defined in any of the above, wherein the optical disposable speculum comprises suction means for extracting fluids.

It is a further object of the present invention to disclose the system as defined in any of the above, wherein the optical disposable speculum comprises means for preventing the collapse of the cervix wall.

It is a further object of the present invention to disclose the system as defined in any of the above, wherein the optical disposable speculum comprises means for providing a continues or pulsed flow of gas for removal of any liquids that may occlude the image acquisition system.

It is a further object of the present invention to disclose the system as defined in any of the above, wherein said image acquisition system further comprises a zoom lens that can be implemented by using a miniature piezo or electric motor.

It is a further object of the present invention to disclose the system as defined in any of the above, wherein the image acquisition system further comprises at least one of automatic, semi-automatic and manual illumination LEDs and a laser diode (LD) adjustment.

It is a further object of the present invention to disclose the system as defined in any of the above, wherein said image acquisition system comprises a sensor imaging system selected from the group consisting of single sensor imaging systems and dual sensor imaging systems, said sensor imaging system comprising at least one element selected from the group consisting of color CMOS, monochrome CMOS, color CCD, and monochrome CCD and an illumination system based on one of LEDs or laser diode (LD). In some embodiments, said illumination system comprises a light source selected from the group consisting of (a) a source for making fluorescence or autofluorescence measurements selected from the group consisting of a UV LED source and a multi-spectral source, (b) an infrared source, and (c) any combination of the above.

In some embodiments, the illumination system comprises a source of white/monochromatic LEDs positioned near a lens aperture in order to optimize the delivery of light into the target tissue with minimum angle of incidence to optimize the reflection from the tissue using a second part of an objective lens. In some embodiments, said illumination system comprises a light source having one of an external strobe or camera electronic shutter to control the camera exposure time and prevent any saturation in the imaging system.

It is a further object of the present invention to disclose the system as defined in any of the above, wherein the image acquisition system achieves depth perception in an acquired image by using at least one of a large depth of field, a continues zoom feature to receive a sequence of different images of the same X, Y position at different focal planes, and dark field illumination applied at different illumination angles using a source of external illumination system.

It is a further object of the present invention to disclose the system as defined in any of the above, wherein said image acquisition system comprises a camera apparatus for obtaining fluorescence images, said camera apparatus comprising a camera, a lens attached to said camera, and a dichroic mirror that transmits UV and reflects visible and IR light.

It is a further object of the present invention to disclose the system as defined in any of the above, wherein said image acquisition system comprises a camera apparatus for obtaining fluorescence images, said camera apparatus comprising a camera, a lens attached to said camera, a UV source in the Bright Field (BF); and, a long pass filter at wavelength of about 400 nm.

It is a further object of the present invention to disclose the system as defined in any of the above, further comprising a detector for detecting stray light generated by improper assembly of the optical disposable speculum to the image acquisition system.

It is a further object of the present invention to disclose the system as defined in any of the above, wherein said detector is a separate unit or one of said sensors.

It is a further object of the present invention to disclose the system as defined in any of the above, wherein said system is utilized in hysteroscopy procedures.

It is a further object of the present invention to disclose a system for direct imaging, diagnosing and (optionally) removing abnormal cells in a target tissue, comprising a disposable speculum; an image acquisition system comprising a plurality of optical elements arranged to capture at least one of a single image or multiple images or video of cells within the target tissue using at least one of bright field or dark field source divided into independently operated segments to obtain a plurality of data sets, said optical elements slidably mounted to a track and in mechanical connection with a sliding mechanism that provides independent motion to each of said optical elements, said image acquisition system assembled on and mechanically secured to an interior surface of said disposable speculum; and an image analysis and control unit in communication with the image acquisition system, the image analysis and control unit analyzing the data sets and applying algorithms to the data sets for diagnosing abnormal cells.

In some embodiments, the speculum comprises at least one selected from a group consisting of means for preventing the collapse of the cervix wall, suction means for extracting fluids, means for providing a continues or pulsed flow of gas for removal of any liquids that may occlude the image acquisition system and any combination thereof.

In some embodiments the speculum comprises a distal end and a proximal end, the interior of which is configured to accommodate an optical apparatus and to keep the optical apparatus centered with respect to the longitudinal axis of the camera housing. The speculum further comprises two rigid blade members characterized by a closed configuration and at least one open configuration, comprising an upper blade member pivotably and slidably mounted to the distal end of the camera housing, and a lower blade member mounted to the camera housing. The upper blade member comprises an arc design for easy access to working tools via the working channel. The lower blade is capable of moving independently of the upper blade.

In some embodiments, the image acquisition system has three separate and independent illuminations: White/Monochromatic/UV/RGB and IR Bright Field (BF) Illumination, White/Monochromatic/RGB Dark Field (DF) illumination for diffusive illumination and divided into segments for independent operation, UV LED for Fluorescence located behind a dichroic mirror, and Bright Field (BF) multi spectral illumination.

In some embodiments, the image acquisition system includes one or more high resolution imaging sensors which capture different wavelength images of a whole field of the target tissue, wherein the images are transmitted to separate channels of said image analysis and control unit and presented separately on a screen.

In some embodiments, the image acquisition system further comprises a laser ablation module with a 2-D moveable mirror system to enable accurate ablation of abnormal cells, wherein said laser ablation module uses said data sets to eliminate the diagnosed abnormal cells, and the image acquisition system is designed to stop ablation when it is detected that abnormal cells no longer exist in the image.

In some embodiments, the laser ablation module comprises a pulsed laser beam selected from the group consisting of infrared laser beam, green laser beam, and ultraviolet laser beam, said laser beam guided via a high power fiber to said target tissue using an imaging lens for focusing said pulse beam with sufficient pulse energy and pulse peak power to remove abnormal cells.

In some embodiments, the image acquisition system further comprises a zoom lens that can be implemented by using a miniature piezo or electric motor.

In some embodiments, the image acquisition system further comprises at least one of automatic, semi-automatic and manual illumination LEDs and a laser diode adjustment.

In some embodiments, the image analysis and control unit is integrated within said image acquisition system.

In some embodiments, the system is utilized in hysteroscopy procedures.

In some embodiments, the said sliding mechanism comprises at least one motor. In some embodiments, the disposable optical speculum covers an optical head and yet enables a free working channel for taking a manual biopsy. In some embodiments, the system comprises a single-use disposable speculum and a multiple-use image acquisition system. In some embodiments, the system comprises a locking mechanism between the optical disposable speculum and the image acquisition system to assure image acquisition without distortions. In some embodiments, the optical disposable speculum integrates a light collimation element guide for dark field illumination with an optical window. In some embodiments, the optical disposable speculum comprises a unique RFID tag to identify said optical disposable speculum.

It is a further object of this invention to disclose a system for direct imaging and diagnosing of abnormal cells in a target tissue, comprising a laparoscope; an image acquisition system comprising a plurality of optical elements arranged to capture at least one of a single image or multiple images or video of cells within the target tissue using at least one of bright field or dark field source divided into independently operated segments to obtain a plurality of data sets, said optical elements slidably mounted to a track and in mechanical connection with a sliding mechanism that provides independent motion to each of said optical elements, said image acquisition system assembled on and mechanically secured to said laparoscope; and an image analysis and control unit in communication with the image acquisition system, the image analysis and control unit analyzing the data sets and applying algorithms to the data sets for diagnosing abnormal cells.

In some embodiments, said sliding mechanism comprises at least one motor. In some embodiments, the laparoscope comprises a locking mechanism between the laparoscope and the image acquisition system to assure image acquisition without distortions. In some embodiments, said laparoscope integrates a light collimation element guide for dark field illumination with an optical window.

It is a further object of this invention to disclose a method for direct imaging, diagnosing and removing abnormal cells in a target tissue, comprising steps of: (a) obtaining (i) an image acquisition system comprising a plurality of optical elements arranged to capture at least one of a single image or multiple images or video of cells within the target tissue using at least one of bright field or dark field source divided into independently operated segments to obtain a plurality of data sets, said optical elements slidably mounted to a track and in mechanical connection with a sliding mechanism that provides independent motion to each of said optical elements; (ii) an image analysis and control unit; (b) communicating said image analysis and control unit with said image acquisition system; and, (c) analyzing the data sets and applying algorithms to the data sets for diagnosing abnormal cells.

It is a further object of this invention to disclose the method as defined above, utilized in hysteroscopy procedures.

It is a further object of this invention to disclose the method as defined above, wherein said sliding mechanism comprises at least one motor.

It is a further object of this invention to disclose the method as defined above, wherein the image acquisition system has three separate and independent illuminations: White/Monochromatic/IR and UV Bright Field (BF) Illumination, White/Monochromatic Dark Field (DF) illumination for diffusive illumination and divided into segments for independent operation, UV LED located behind a dichroic mirror for Fluorescence, and Bright Field (BF) multi spectral illumination.

It is a further object of this invention to disclose the method as defined above, wherein the image acquisition system includes one or more high resolution imaging sensors which capture different wavelength images of a whole field of the target tissue, wherein the images are transmitted to separate channels of said image analysis and control unit and presented separately on a screen.

It is a further object of this invention to disclose the method as defined above, wherein the image acquisition system further comprises a laser ablation module with a 2-D moveable mirror system to enable accurate ablation of abnormal cells, wherein said laser ablation module uses said data sets to eliminate the diagnosed abnormal cells, and the image acquisition system is designed to stop ablation when it is detected that abnormal cells no longer exist in the image.

It is a further object of this invention to disclose the method as defined above, wherein the laser ablation module comprises a pulsed laser beam selected from the group consisting of infrared laser beam, green laser beam, and ultraviolet laser beam, said laser beam guided via a high power fiber to said target tissue using an imaging lens for focusing said pulse beam with sufficient pulse energy and pulse peak power to remove abnormal cells.

It is a further object of this invention to disclose the method as defined above, wherein said system is an optical disposable speculum; further wherein said optical disposable speculum comprises an optical window provided with a layer of elastic material disposed so as to prevent stray light from entering said image acquisition system.

It is a further object of this invention to disclose the method as defined above, wherein said speculum comprises at least one selected from a group consisting of means for preventing the collapse of the cervix wall, suction means for extracting fluids, means for providing a continues or pulsed flow of gas for removal of any liquids that may occlude the image acquisition system and any combination thereof.

It is a further object of this invention to disclose the method as defined above, wherein said image acquisition system further comprises a zoom lens that can be implemented by using a miniature piezo or electric motor.

It is a further object of this invention to disclose the method as defined above, wherein the image acquisition system further comprises at least one of automatic, semi-automatic and manual illumination LEDs and a laser diode adjustment.

It is a further object of this invention to disclose the method as defined above, wherein said image acquisition system comprises a sensor imaging system selected from the group consisting of single sensor imaging systems and dual sensor imaging systems, said sensor imaging system comprising at least one element selected from the group consisting of color CMOS, monochrome CMOS, color CCD, and monochrome CCD; and, an illumination system based on one or more of LEDs or laser diode.

It is a further object of this invention to disclose the method as defined above, wherein said illumination system comprises: bright field illumination; dark field external source illumination; and, a light source selected from the group consisting of (a) a source for making fluorescence or autofluorescence measurements selected from the group consisting of a UV LED source and a multi-spectral source, (b) an infrared source, and (c) any combination of the above.

It is a further object of this invention to disclose the method as defined above, wherein the illumination system comprises a source of white/monochromatic/IR and UV fluorescence LEDs positioned near a lens aperture in order to optimize the delivery of light into the target tissue with minimum angle of incidence to optimize the reflection from the tissue using a second part of an objective lens.

It is a further object of this invention to disclose the method as defined above, wherein the image acquisition system achieves depth perception in an acquired image by using at least one of a large depth of field, a contiguous zoom feature to receive a sequence of different images of the same X, Y position at different focal planes, and dark field illumination applied at different illumination angles using a source of external illumination system.

It is a further object of this invention to disclose the method as defined above, wherein said image acquisition system comprises a camera apparatus for obtaining fluorescence images, said camera apparatus comprising: a camera; a lens attached to said camera; and, a dichroic mirror that transmits UV and reflects visible and IR light.

It is a further object of this invention to disclose the method as defined above, wherein said image acquisition system comprises a camera apparatus for obtaining fluorescence images, said camera apparatus comprising: a camera; a lens attached to said camera; a UV source in the Bright Field (BF); and, a long pass filter at wavelength of about 400 nm.

It is a further object of this invention to disclose the method as defined above, wherein said image acquisition system comprises a light source having one of an external strobe or camera electronic shutter to control the camera exposure time and prevent any saturation in the imaging system.

It is a further object of this invention to disclose the method as defined above, further comprising a detector for detecting stray light generated by improper assembly of the optical disposable speculum to the image acquisition system.

It is a further object of this invention to disclose the method as defined above, wherein said image analysis and control unit is integrated within said image acquisition system.

BRIEF DESCRIPTION OF THE DRAWINGS

The invention will now be described with reference to the drawings, wherein.

DETAILED DESCRIPTION

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The term "SpeculuView" system refers hereinafter to an apparatus comprising a disposable optical speculum and an image acquisition system comprising a treatment module and an image analysis and control unit. Thus, according to one embodiment, the term "SpeculuView" is a gynoscope.

The term "Gynoscopy" system refers hereinafter to a cervix imaging procedure.

The term "hysteroscopy" refers hereinafter to the inspection of the uterine cavity by endoscopy with access through the cervix. It allows for the diagnosis of intrauterine pathology and serves as a method for surgical intervention (operative hysteroscopy).

The system described herein may be used for imaging in gynecology daily procedure exams, surgical procedures, colposcopy laparoscopy or hysteroscopy. In some embodiments, it comprises a treatment module for ablation of abnormal cells (e.g. cancerous cells) in the examined area (e.g. the uterine cervix).

One of the aims of the SpeculuView system is to provide an apparatus that enables the user to perform detailed, high-resolution observation of objects located within a relatively wide area (e.g. the uterine cervical cavity) and accurate ablation of abnormal cells (e.g. cancerous cells in the uterine cervix).

One of the advantages of the SpeculuView system is the Optional BF with PBS (polarized beam splitter) or BS with one (optional variable) polarizer near the illumination source and one polarizer near the sensor, instead of direct BF near the aperture or simple BS (Beam Splitter) allow cross polarization option for edge enhancement technique.

It should be emphasized that the present invention can also be utilized in hysteroscopy procedures. In such procedures the image acquisition system can be utilized to perform direct imaging, diagnosing and treatment within the uterus.

Figure 1A:
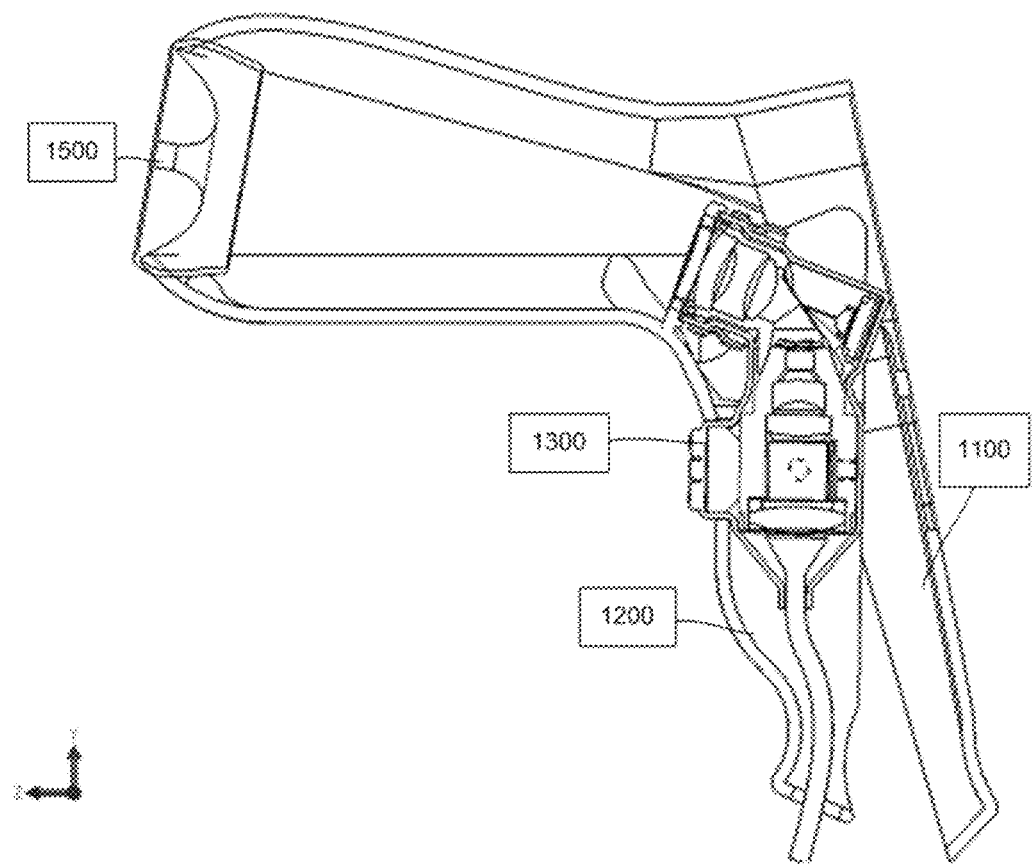
FIG. 1A presents an assembled view of the system herein disclosed, including an exemplary area inspected by the system.
Figure 1B:
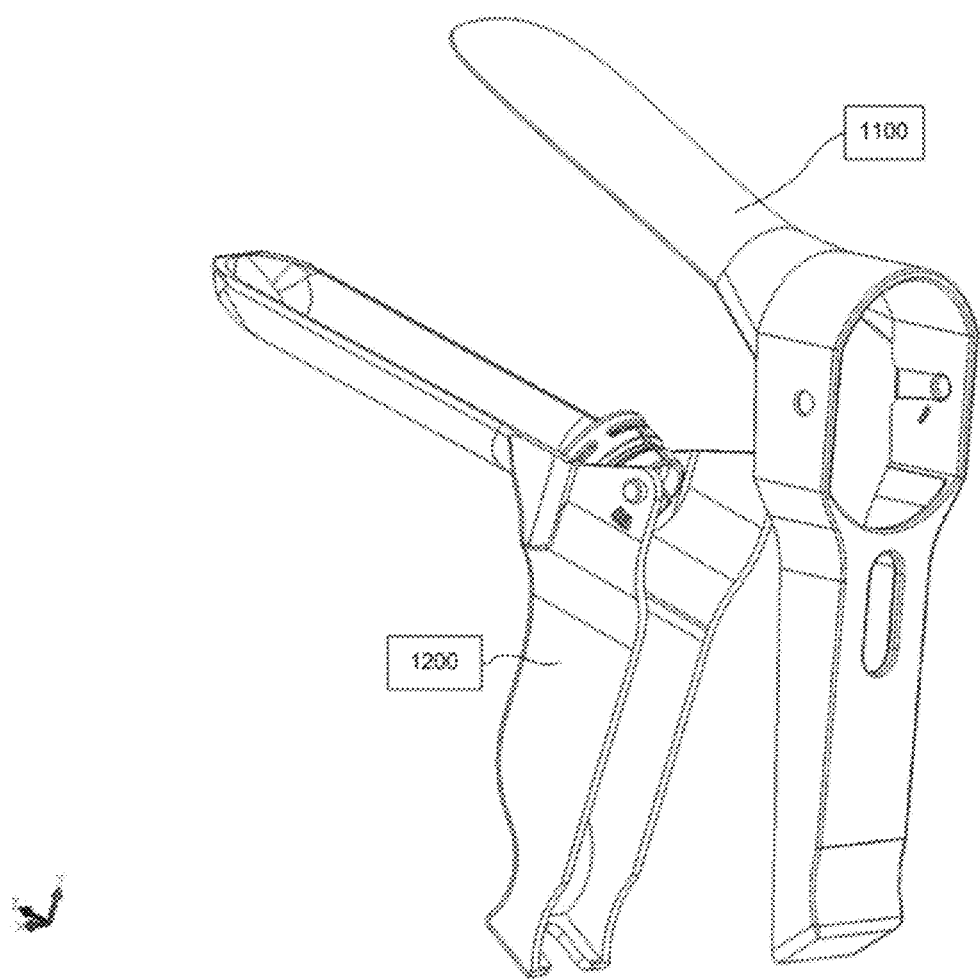
FIG. 1B presents an exploded view of the system herein disclosed.

In the SpeculuView system, a disposable optical speculum is assembled on the image acquisition system on each examination. The disposable speculum creates a clean environment for the image acquisition system, preventing it from being contaminated and preventing cross-contamination of the patient, physician (e.g., the gynecologist), assisting nurse or any combination. Reference is now made to FIG. 1A, which shows an assembly cross section view of one embodiment of the SpeculuView system, including the inspection area, and including an example of a possible inspected area, the uterine cervix. Shown in the figure are a cross sectional view 1100 of the upper part of the disposable optical speculum; a cross sectional view 1200 of the lower part of the disposable optical speculum; a cross sectional view 1300 of the image acquisition system; and a cross sectional view 1500 of the uterine cervix, as a non-limiting example of an area examined by the system. Reference is now made to FIG. 1B, which shows an exploded view of one embodiment of the disposable optical speculum, showing upper part 1100 and lower part 1200. The design of the system herein disclosed enables a shortened time between examinations compared with designs known in the art.

Figure 2A:
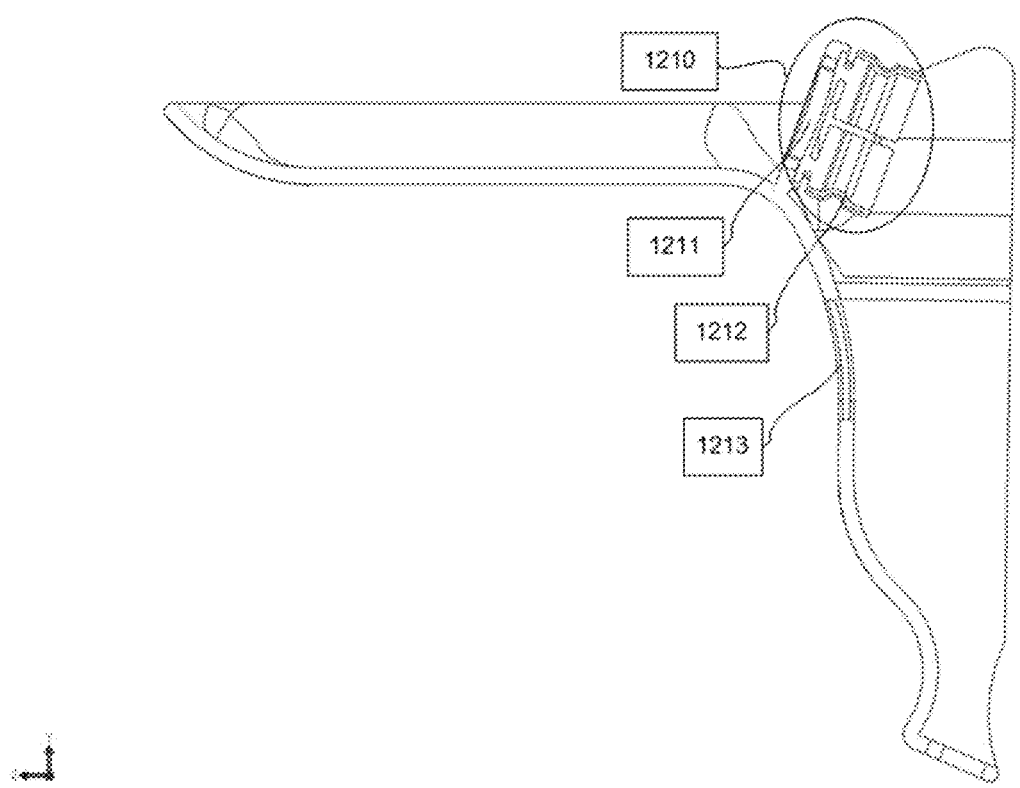
FIG. 2A presents a cross-sectional view of the design of one embodiment of the cover window in the lower part of the disposable optical speculum.

Reference is now made to FIG. 2A, which shows a cross sectional view 1210 of the design of one embodiment of the cover window in the lower part of the disposable optical speculum. The figure illustrates the front window lens area 1211; breakable snap attachments for the image acquisition system 1212; and a cut release 1213 for the operating buttons. In the embodiment of the system illustrated in FIG. 2B, the image acquisition system is attached to the speculum via breakable snaps 1212 that break after the optical imaging system is detached from the speculum. The use of an embodiment comprising these breakable snaps ensures that a new disposable speculum will be used for each use of the system, since it will not be possible to insert the image acquisition system into a speculum that has already been used once.

Figure 2B:
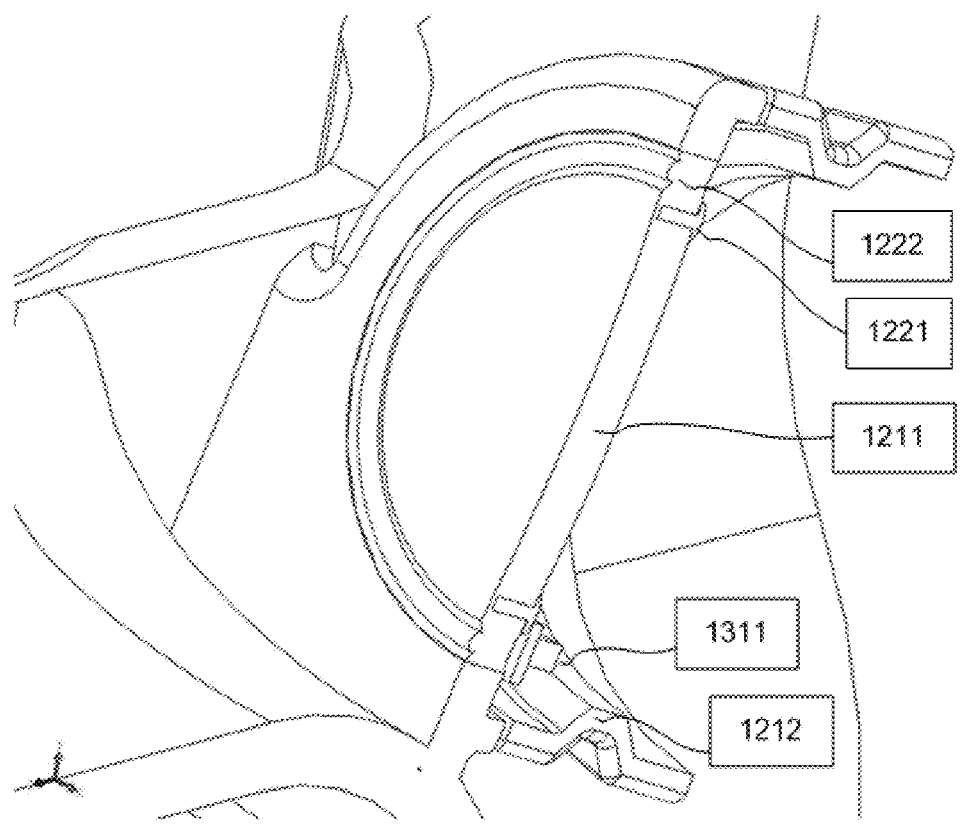
FIG. 2B provides a close-up view of the front window lens shown in FIG. 2A.

Reference is now made to FIG. 2B, which provides a close-up view 1211 of the front window lens shown in FIG. 2A. The view shown in FIG. 2B includes a linear cylindrical collimating lens 1222 for a dark field LED source in the image acquisition system; an elastic layer 1221 for blocking stray light entering the image acquisition system (e.g. from dark field illumination or bright field illumination); and dark field illumination LED source 1311. In some embodiments of the invention, in order to prevent stray light from entering the image acquisition system (described in detail below), the window of the optical speculum is provided with a layer of elastic material 1221 that creates a fine-tuned coupling between the optical speculum and the image acquisition system. The layer of elastic material compensates for slight manufacturing or assembly mismatches between the other optical components.

The image acquisition system comprises bright field and dark field illumination and uses a LED source. Any LED or laser diode that can produce narrow band spectrum can be used for hyper spectral imaging may be used. As non-limiting examples, a UV LED source may be used (e.g. for fluorescence and/or autofluorescence measurements). As a second non-limiting example, a laser diode may be used.

Figure 3:
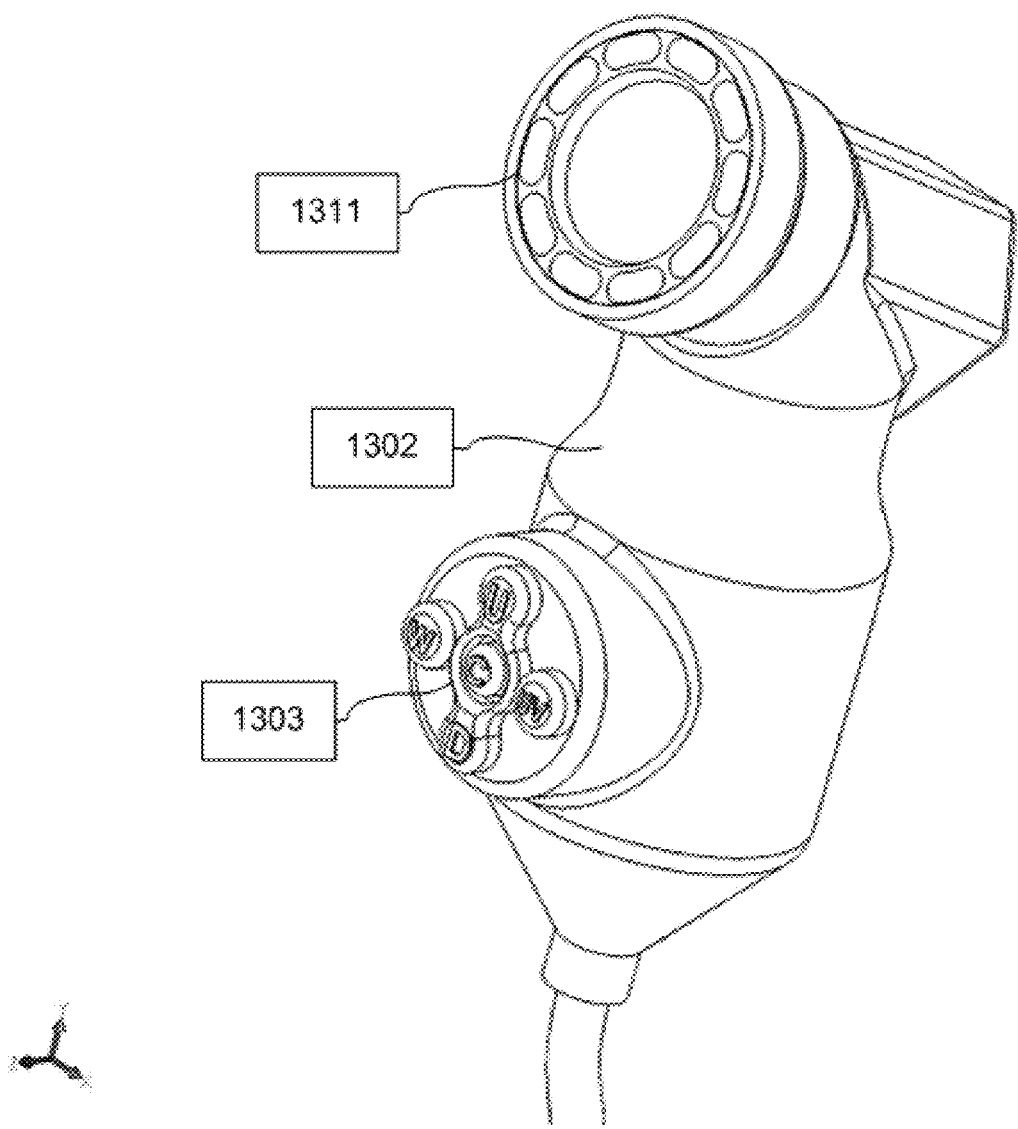
FIG. 3 presents a schematic illustration of one embodiment of the image acquisition system.
Figure 4:
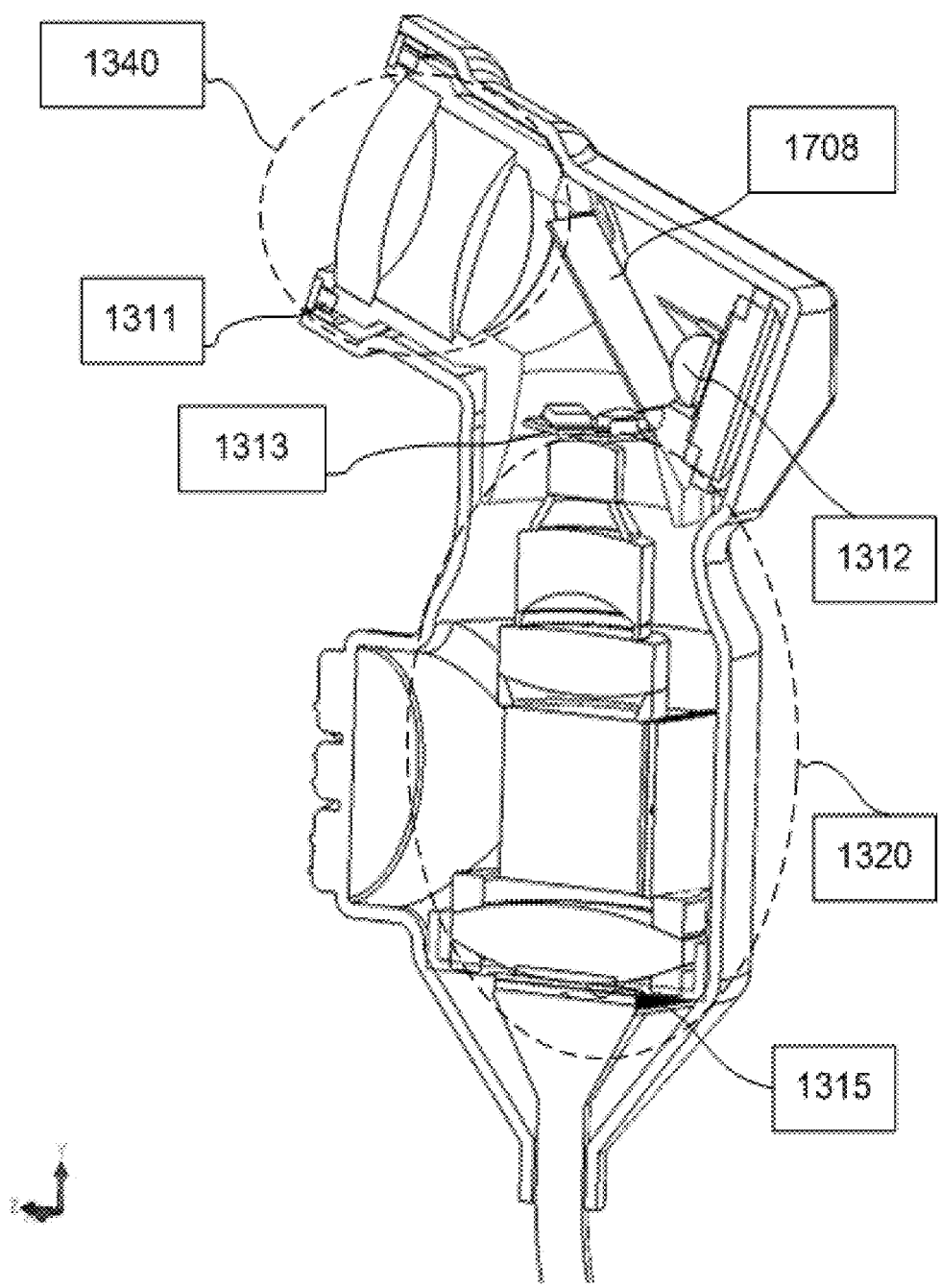
FIG. 4 presents a cross-sectional view of the image acquisition system of FIG. 3.

A LED with output in the visible (single wavelength or white) or IR may be used as well. The IR source is used in embodiments in which in depth detection is desired. Reference is now made to FIGS. 3 and 4, which present schematic illustrations of one embodiment of the image acquisition system. FIG. 3 presents an external view, showing the body 1302 of the image acquisition system, camera head operating buttons 1303, and the dark field illumination LED source 1311. An internal view of this embodiment is shown in FIG. 4, which shows the dark field illumination LED source 1311; LEDs 1312; bright field illumination LED source 1313; imaging sensor area 1315; dichroic mirror 1708; and two groups of optical components that together comprise the objective lens system of the image acquisition system, front lens group 1340 and rear lens group 1320.

In some embodiments of the invention, group 1320 (see FIG. 4) is connected to the imaging sensor and a beam splitter and/or dichroic mirror, and includes the aperture stop where the bright field illumination components are nearly located. In some embodiments of the invention, group 1340 (see FIG. 4) includes a group of optical elements along with the disposable optical window 1211 (see FIG. 2A).

In some embodiments of the invention, particularly those in which fluorescence or autofluorescence measurements are made; dichroic mirror 1708 (see FIG. 4) is located between groups 1320 and 1340. The bright field light source is located near the dichroic mirror. In some embodiments, the multi-spectral, white, or UV light source is located on the other side of the dichroic mirror along the objective axis of group 1340.

In a preferred embodiment, the illumination system comprises a UV LED light source for fluorescence image analysis in addition to bright and dark field white light sources. It is well-known in the art that cancerous cells are highly emphasized by this kind of illumination. In these embodiments, the optical design comprises a dichroic mirror that transmits light of the UV LED with λ<400 nm and reflects light of the other light sources with λ>440 nm.

Figure 5:
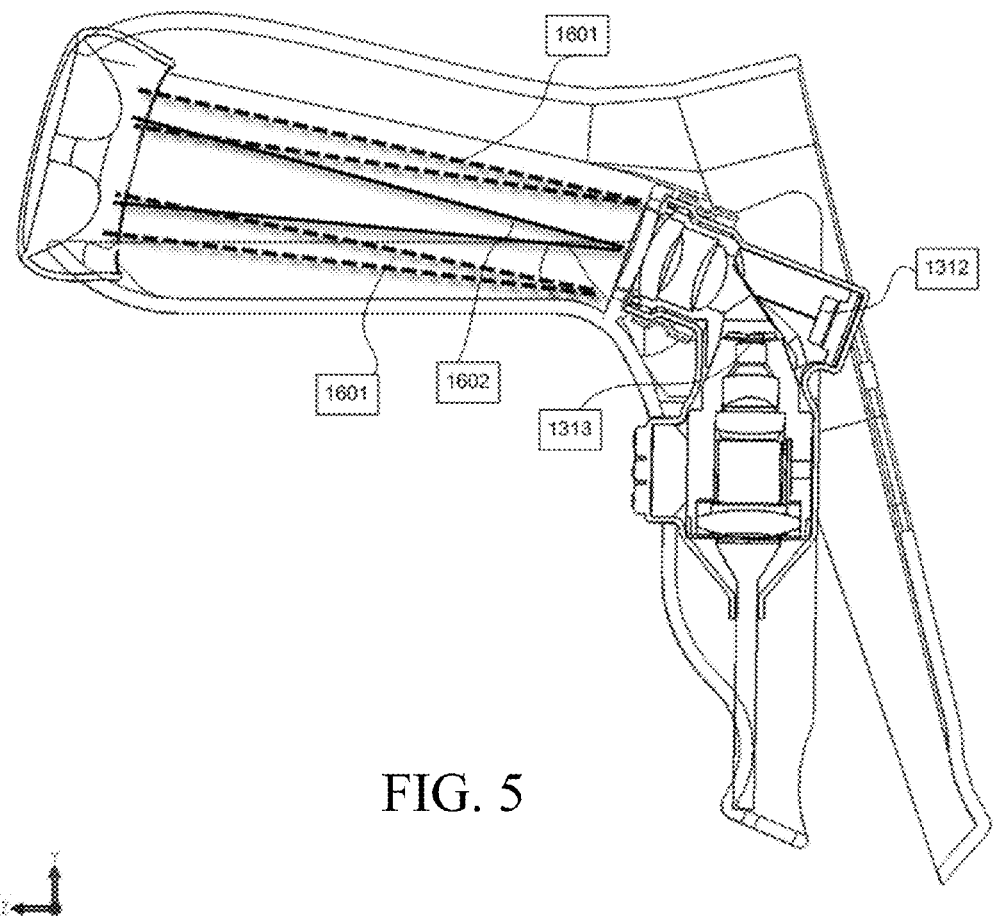
FIG. 5 presents a partial ray-tracing diagram illustrating the bright field and dark field illumination provided by one embodiment of the system.

Reference is now made to FIG. 5, which presents a ray-tracing diagram of the illumination provided by one embodiment the image acquisition system. Superimposed on a cross-sectional view of the system (an optical speculum assembled around an image acquisition system) are lines illustrating the dark field (1601) and bright field (1602) illumination rays.

Preferred embodiments of the system comprise one of two image acquisition designs: a single imaging sensor system comprising a color CMOS or CCD and an illumination system based on LEDs or laser diodes (LDs), or a dual imaging sensor system comprising two different CMOS or CCDs, (in some embodiments, one color and one monochrome), and an illumination system based on LEDs or LDs.

Figure 6A:
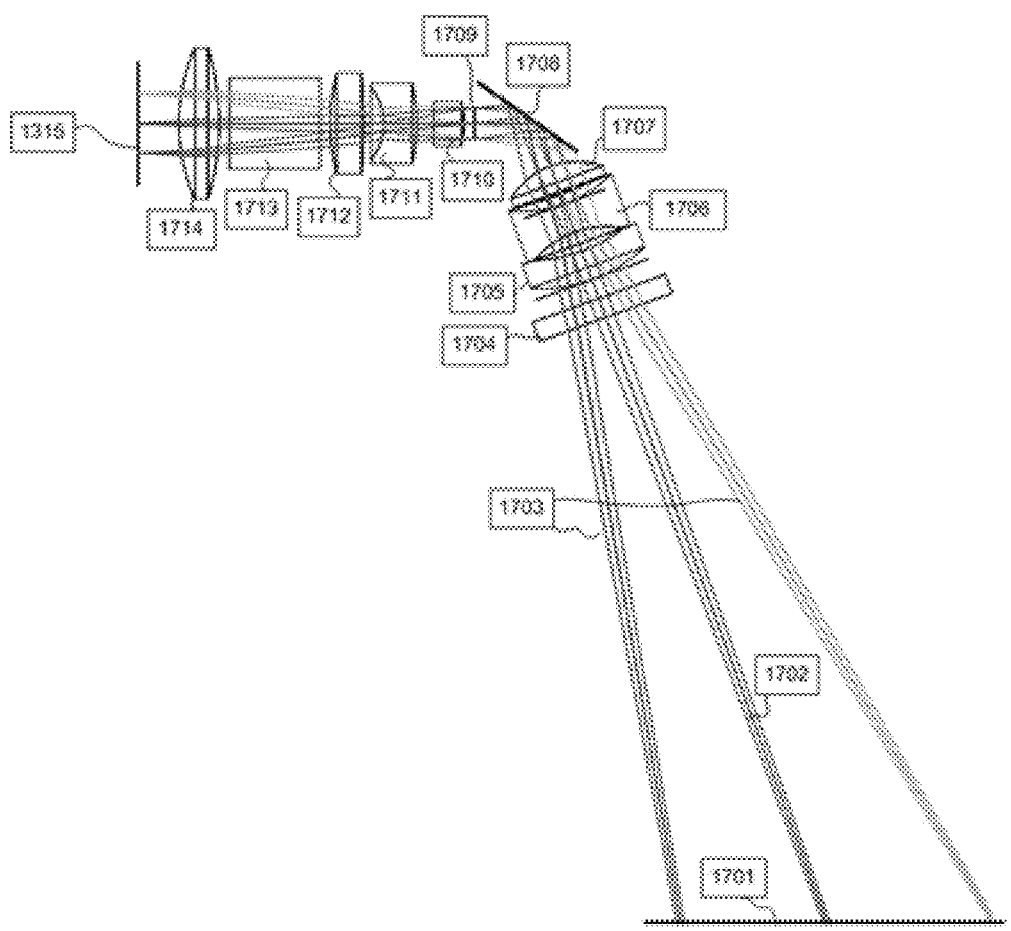
FIG. 6A presents an illustration of the optical design and chief rays for one embodiment of a system comprising a single imaging sensor.
Figure 6B:
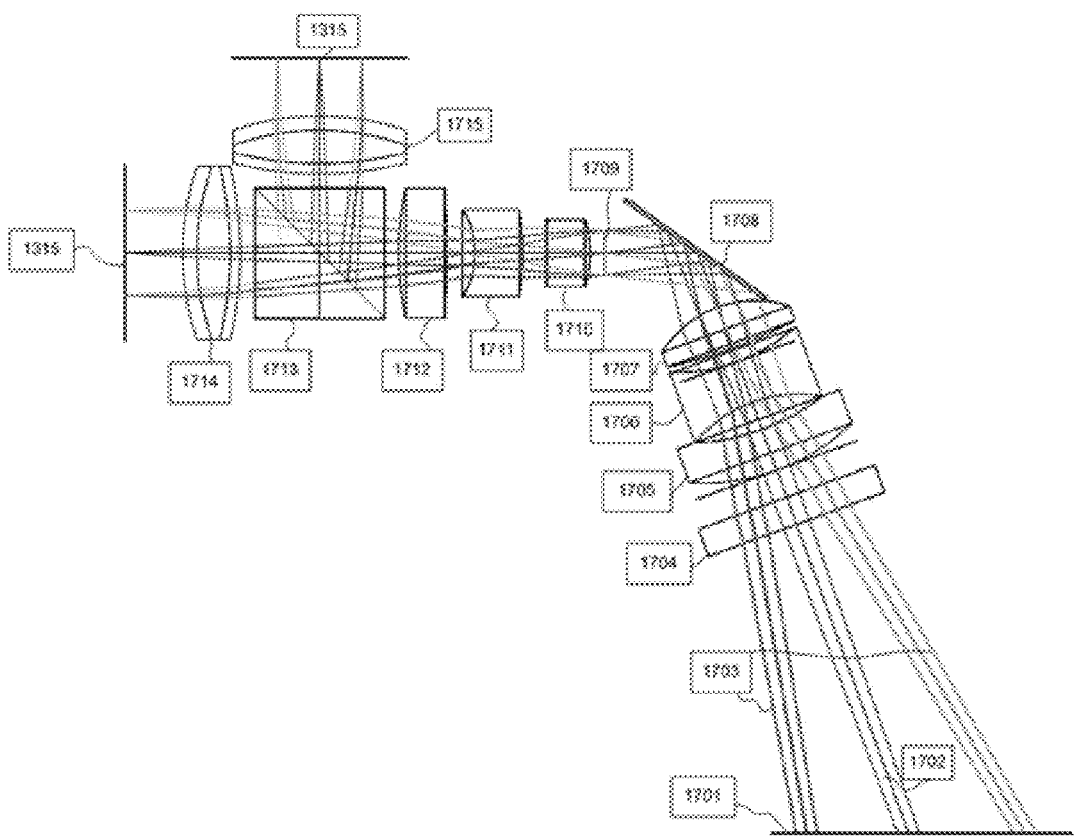
FIG. 6B presents an illustration of the optical design and chief rays for one embodiment of a system comprising a system comprising dual imaging sensor.

Reference is now made to FIGS. 6A and 6B, which schematically illustrate two embodiments of optical designs for use in an optical head of an image acquisition system for viewing internal cavities (e.g., uterine cervix). Non-limiting examples of uses of the image acquisition system include video laparoscopy, which is enabled by the use of a special optical adapter assembled on the image acquisition system, and detection of abnormal cells in a laparoscopy procedure.

Reference is now made to FIG. 6A, which presents an illustration of the optical design and chief rays for one embodiment of a system comprising a single imaging sensor. Shown in the illustration are the area being examined (1701); optical elements comprising window 1704, first meniscus element 1705, bi-concave element 1706, first bi-convex element 1707, dichroic mirror 1708, aperture 1709, plano-convex element 1710, second meniscus element 1711, second bi-convex element 1712, beamsplitter 1713, (bi-convex) focusing element 1714, and imaging sensor 1315; and the chief (1702) and marginal (1703) return rays.

Reference is now made to FIG. 6B, which presents an illustration of the optical design and chief rays for one embodiment of a system comprising a system comprising dual imaging sensor. Shown in the illustration are the area being examined (1701); optical elements comprising window 1704, first meniscus element 1705, bi-concave element 1706, first bi-convex element 1707, dichroic mirror 1708, aperture 1709, plano-convex element 1710, second meniscus element 1711, second bi-convex element 1712, beamsplitter 1713, (bi-convex) first focusing element 1714a, first imaging sensor 1315a, (bi-convex) second focusing element 1714b, and second imaging sensor 1315b; and the chief (1702) and marginal (1703) return rays.

Figure 7A:
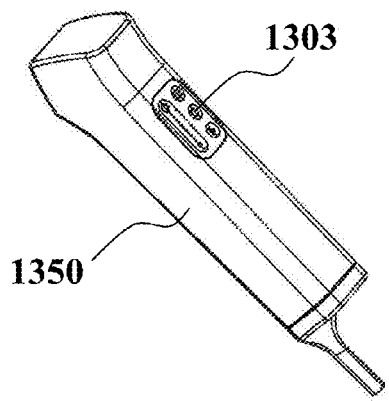
FIG. 7A shows an exterior view of one embodiment of the camera housing.
Figure 7B:
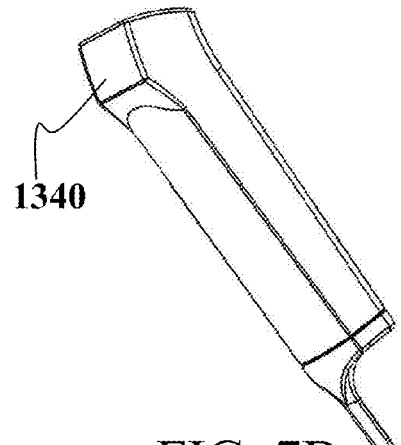
FIG. 7B shows another exterior view of one embodiment of the camera housing.
Figure 7C:
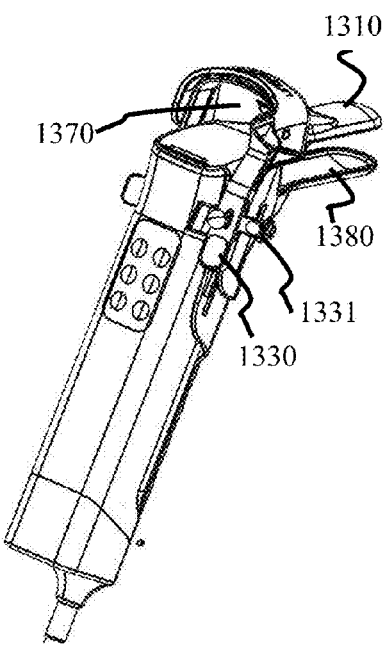
FIG. 7C shows a view of how the camera housing is integrated into the disposable speculum and the operating mechanism of the disposable speculum.
Figure 7D:
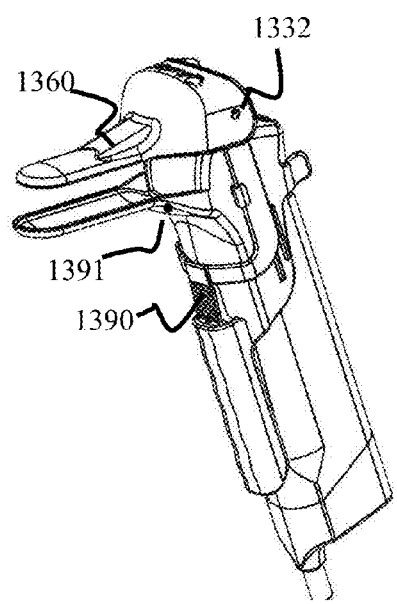
FIG. 7D shows another view of how the camera housing is integrated into the disposable speculum and the operating mechanism of the disposable speculum.

Reference is now made to FIGS. 7A-7F, which present schematic illustrations of one embodiment of a camera housing 1350 and its integration into the disposable speculum of the present invention. FIG. 7A shows a rear view of the camera housing, illustrating the position of camera operating buttons 1303, and FIG. 7B shows a front view of the camera housing, illustrating front lens 1340. FIGS. 7C and 7D are rear and front views, respectively, of one embodiment of a speculum of the present invention into which a camera housing has been integrated.

FIG. 7C presents the upper blade 1310, lower blade 1380, free working channel 1370 for inserting various tools and examination probes, a pushing lever for the upper blade moving pivotably 1330, and a locking mechanism 1331 for the upper blade. FIG. 7D presents the pivot axis 1332, an arc design 1360 on the upper blade to ensure an easy access for a special working tool via the working channel, a vertical axis for sliding the upper blade up and down 1390, and a fluid drain hole 1391 which can also connect to an extraction tube for active suction.

Figure 7E:
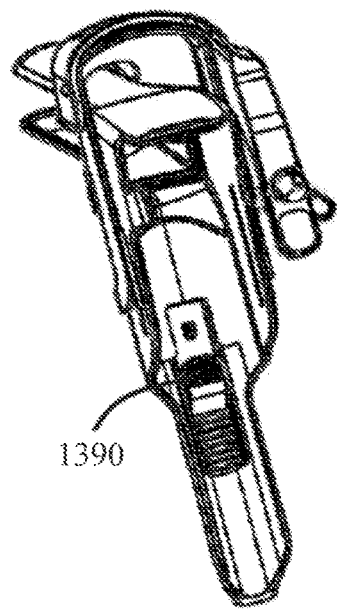
FIG. 7E is a rear view of the disposable speculum.
Figure 7F:
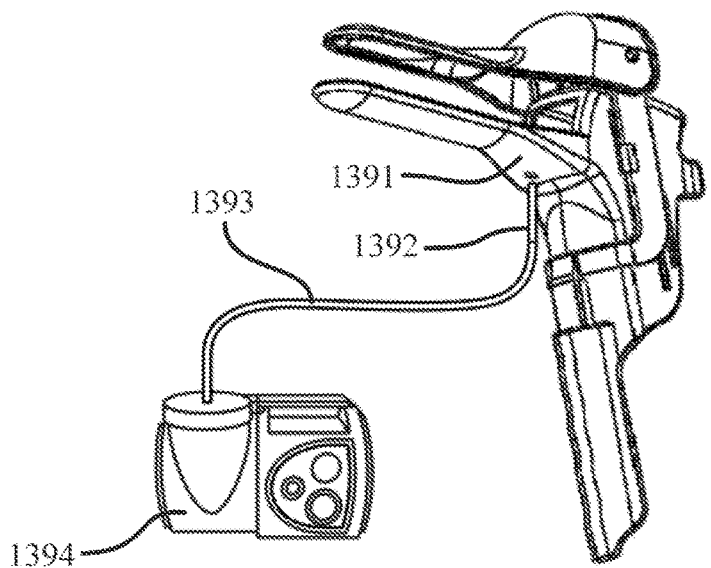
FIG. 7F is a front view of the disposable speculum.

FIG. 7E and FIG. 7F present the disposable speculum in rear and front views, respectively, illustrating a drain hole 1391, for example in the lower speculum blade 1380, a drain adapter 1392 (e.g. luer lock adapter) connecting the drain hole 1391 to an extraction tube 1393, and an example of a medical fluid suction pump 1394. For example, when a gynecologist is applying a fluid such as Aceto-White acid as part of the procedure to verify if the tissue has suspicious areas to take a biopsy, the excess fluid may drain through the drain hole 1391. In other procedures with more fluids, an external fluid suction pump 1394 can be connected to the drain hole.

As such, at least one of the rigid blade members 1310, 1380 comprises at least one fluid transporting member 4103 (see FIG. 7G) connected to a drain hole 1391 provided therein for transporting fluid to or from a location proximal to the camera housing 1350, and at least one extraction tube 1393 secured to the drain hole 1391 for transporting fluid, the extraction tube comprising a proximal end and a distal end, the proximal end fluidly connectable to a fluid or suction source 1394 located proximal to the camera housing. The extraction tube 1393 may pass either through the camera housing 1350 or outside of the camera housing 1350. The fluid transporting member includes at least one channel, at least one tube, or a combination thereof. The fluid transporting member may extend to an end of either one of the rigid blade members 1310, 1380, or may terminate at a location within a volume encompassed by either one of the rigid blade members. In one embodiment, at least a first extraction tube is fluidly attachable to a fluid source and a second extraction tube is fluidly connectable to a suction source, the first extraction tube adapted to transport fluid to at least one of the rigid blade members, and the second extraction tube adapted to withdraw fluid from at least one of the rigid blade members.

Figure 7G:
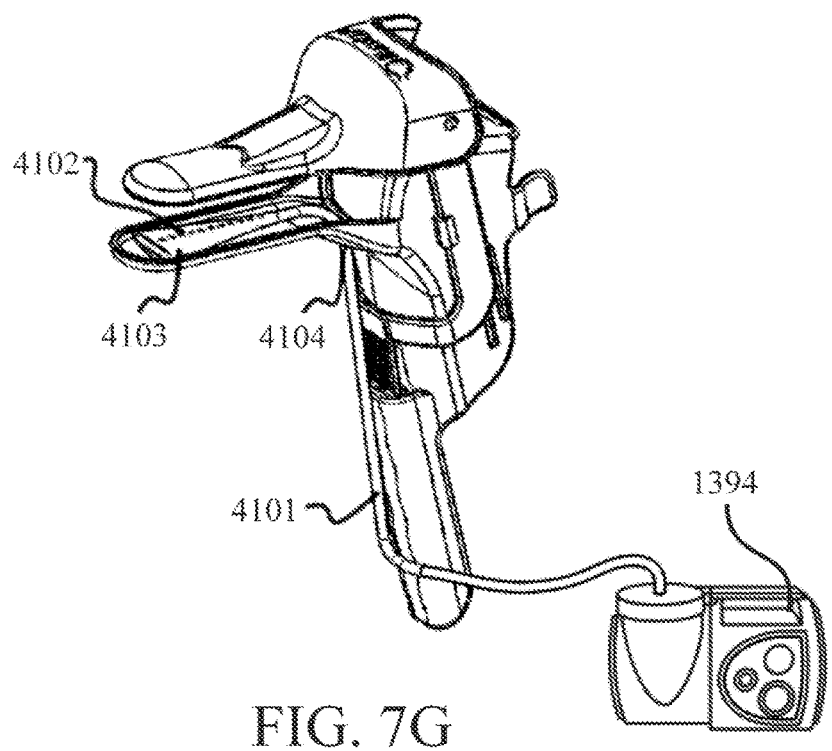
FIG. 7G shows the optical disposable speculum with a suction system for fluid and gas (and/or vapor) during a gynecology procedure.

Reference is now made to FIG. 7G, which illustrate the optical disposable speculum with a suction system for fluid and gas (and/or vapor) during a gynecology procedure. The suction system may include a fluid transporting member 4103 located inside the lower speculum blade 1380 and may include a wide area for fluid suction and/or holes for gas (vapor) suction 4102. The suction system also collects the fluids at the distal end 4104 of the speculum (near the optical lens) to keep the lens clean from fluid. The suction system may be connected to a suction pump at the end of the tube 4101 with a flexible tube.

In some embodiments, the optical design comprises at least one motor perpendicular to the optical system axis moving at least one optical component in two or more stages.

Some embodiments of the system herein disclosed in which it comprises a sliding mechanism are illustrated in FIG. 8 (see 8A-8F). In contrast to embodiments such as those shown in FIGS. 6A and 6B, which have a fixed working distance and magnification, the embodiments shown in FIG. 8 (see 8A-8F), provide for both variable working distance and variable magnification.

Figure 8A:
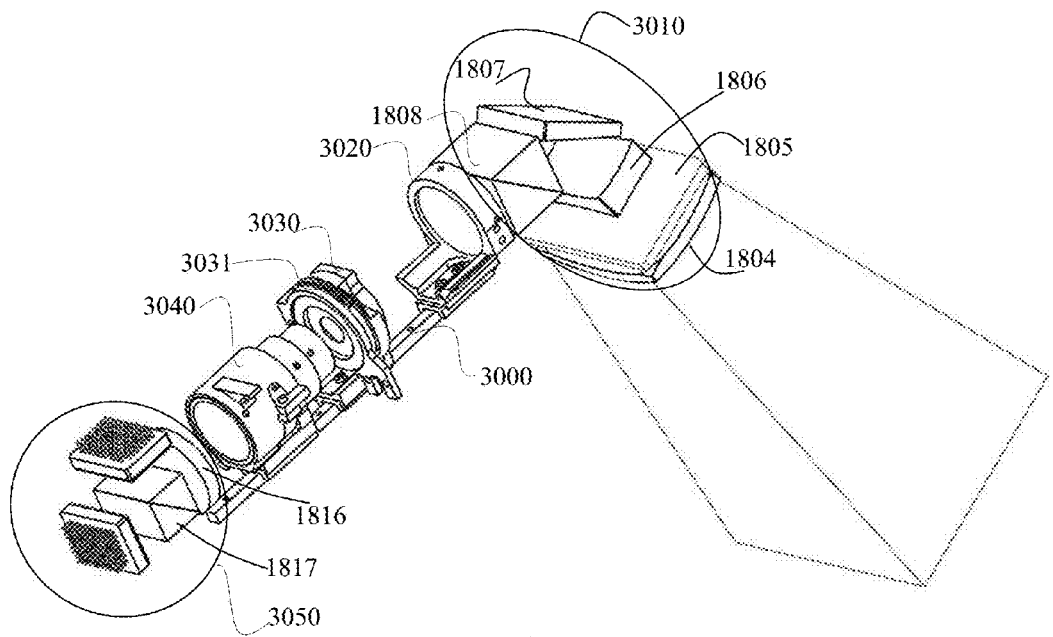
FIG. 8A shows an isometric view of one embodiment of a sliding mechanism designed to allow independent movement of the optical components comprising one and or two imaging sensors for high dynamic imaging capabilities, including an optical train that comprises a sliding mechanism and two imaging sensors design.

Reference is now made to FIG. 8A, which shows an isometric view of one embodiment of an optical train that comprises a sliding mechanism. In the embodiment shown in the figure, the optical train is housed inside of a disposable speculum. In the embodiment illustrated, three movable lens groups (some of which comprise a single lens) are mounted in mounts 3020, 3030, 3040 and 3050. The mounts are slidably mounted to track 3000 which is attached to the speculum. The track allows linear motion of the optic elements while keeping them aligned. Cogwheel 3031 is used to control the diameter of the aperture. In the embodiment shown, each of lens mounts 3020 and 3030 is slidably mounted to track 3000. In preferred embodiments of the system, each lens group can be moved independently of each of the others. In some embodiments of the system, the motion of the lens groups is actuated manually via mechanical connections running from the lens mounts to a point external to the housing (speculum, laparoscope, etc.) In other embodiments of the system, the motion of the lens groups is actuated by the motor or motors mentioned above, each of which is in mechanical connection with the lens mount or mounts that it controls.

Figure 8B:
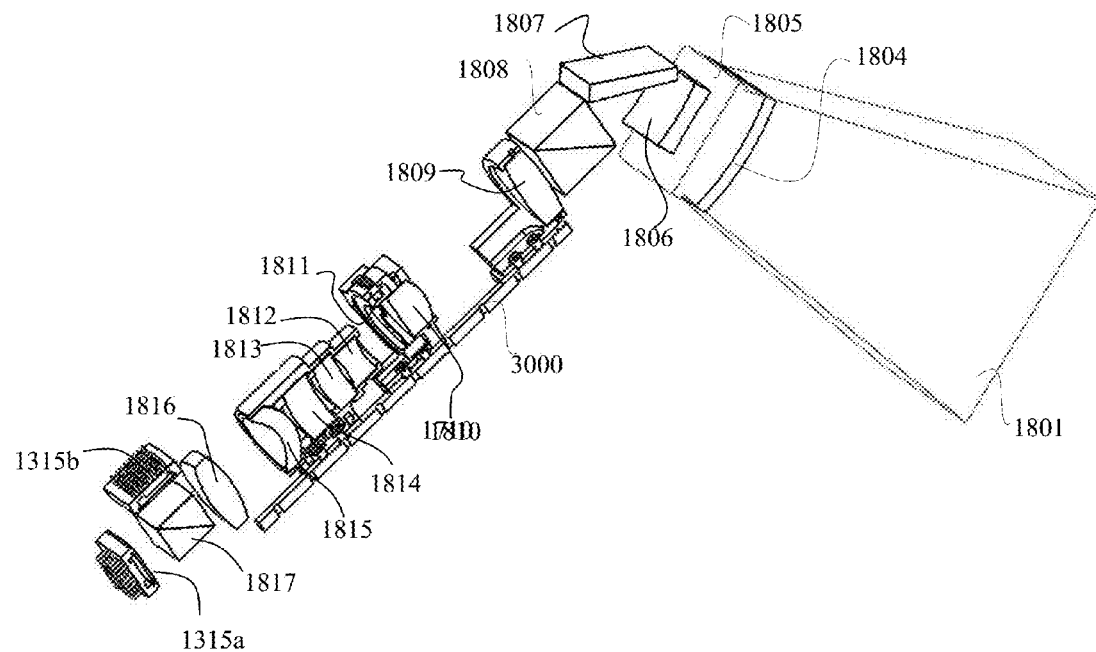
FIG. 8B shows a cross-sectional view of the embodiment illustrated in FIG. 8A.

Reference is now made to FIG. 8B, which shows a cross-sectional view of the embodiment illustrated in FIG. 8A. Shown in FIG. 8B are the area being examined (1801); optical elements comprising Disposable Meniscus window 1804, Protected window 1805, first bi Concave element 1806, Dichroic mirror 1807, Bright field Beam Splitter 1808, bi-convex element 1809, Plano-convex element 1810, aperture 1811, second bi-concave element 1812, Meniscus element 1813, Meniscus element 1815, Bi-Convex 1816, beam splitter 1817, first imaging sensor 1315a, and second imaging sensor 1315b.

It should be emphasized that FIGS. 8A-8B present an illustration of the optical design and for one embodiment of a system comprising a system comprising a dual imaging sensor: a beam splitter and a lens.

FIGS. 8A-8B further comprise two stationary groups represented by numerical references 3010 and 3050.

Numerical reference 3050 represents the dual imaging sensor (1315a and 1315b), Bi-Convex 1816, beam splitter 1817; and numerical reference 3010 comprises a disposable Meniscus window 1804, Protected window 1805, bi Concave element 1806, Dichroic mirror 1807, Bright field Beam Splitter 1808.

Figure 8C:
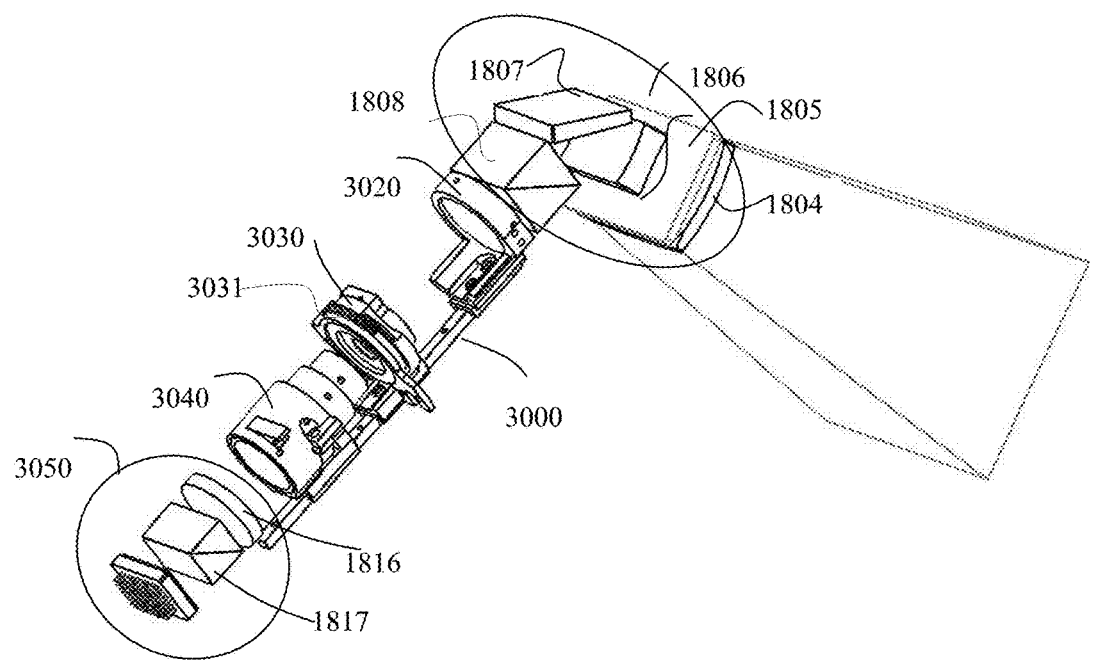
FIG. 8C shows an isometric view of one embodiment of an optical train that comprises a sliding mechanism and one imaging sensors design.
Figure 8D:
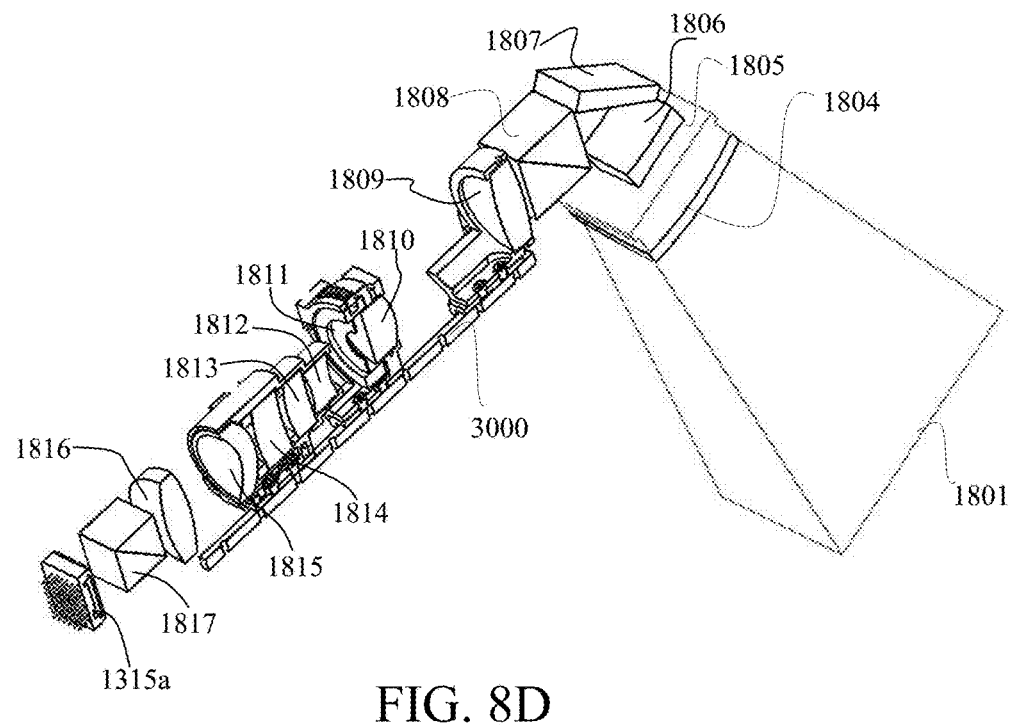
FIG. 8D shows a cross-sectional view of the embodiment illustrated in FIG. 8C.

Reference is now made to FIGS. 8C-8D, which present an illustration of the optical design for one embodiment of a system comprising a single imaging sensor.

Shown in FIGS. 8C-8D are the area being examined 1801; optical elements comprising Disposable Meniscus window 1804, Protected window 1805, first bi Concave element 1806, Dichroic mirror 1807, Bright field Beam Splitter 1808, bi-convex element 1809, Plano-convex element 1810, aperture 1811, second bi-concave element 1812, Meniscus element 1813, Meniscus element 1815, Bi-Convex 1816, beamsplitter 1817 and imaging sensor 1315.

It should be pointed out that FIG. 8D shows a cross-sectional view of the embodiment illustrated in FIG. 8C.

As in the embodiment illustrated in FIGS. 8A-8B, in the embodiment illustrated in FIGS. 8C-8D, three movable lens groups (some of which comprise a single lens) are mounted in mounts 3020, 3030, and 3040. The mounts are slidably mounted to track 3000 which is attached to the speculum. The track allows linear motion of the optic elements while keeping them aligned. Cogwheel 3031 is used to control the diameter of the aperture. In the embodiment shown, each of lens mounts 3020 and 3030 is slidably mounted to track 3000. In preferred embodiments of the system, each lens group can be moved independently of each of the others. In some embodiments of the system, the motion of the lens groups is actuated manually via mechanical connections running from the lens mounts to a point external to the housing (speculum, laparoscope, etc.) In other embodiments of the system, the motion of the lens groups is actuated by the motor or motors mentioned above, each of which is in mechanical connection with the lens mount or mounts that it controls.

Figure 8E:
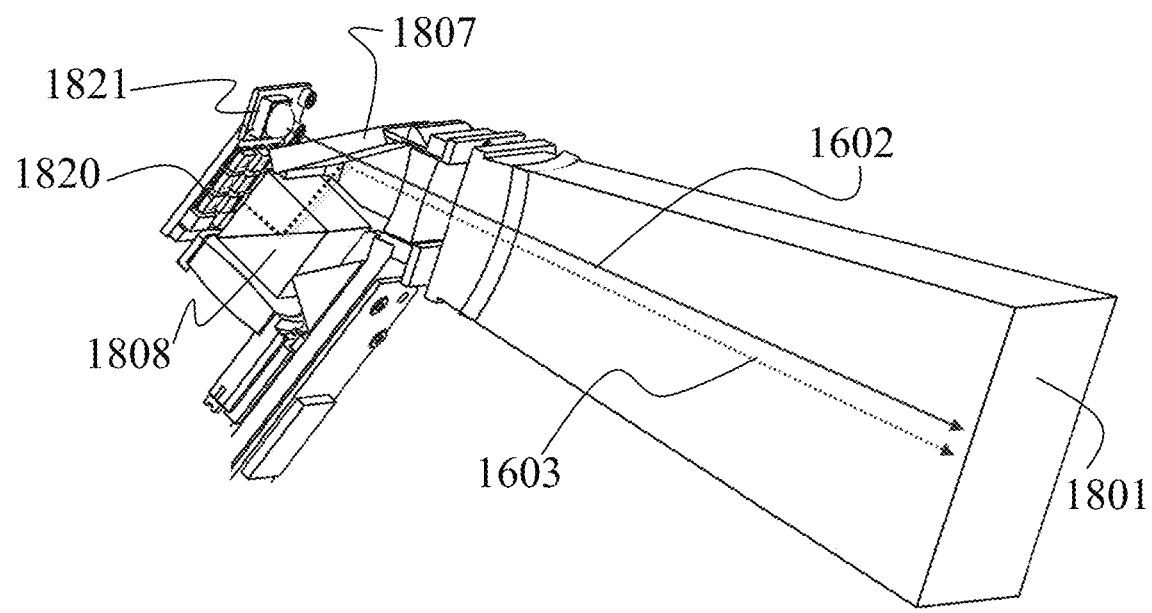
FIG. 8E presents a front view of the distal end of end of the optical system in an embodiment in which it is used for bright field measurements and fluorescence measurements.

Reference is now made to FIG. 8E, which presents a front view of the distal end of end of the optical system in an embodiment in which it is used for fluorescence measurements. Shown are LEDs 1820, dichroic mirror 1807, beamsplitter 1808, and rays illustrating bright field (1603) and fluorescence (1602) radiation.

Figure 8F:
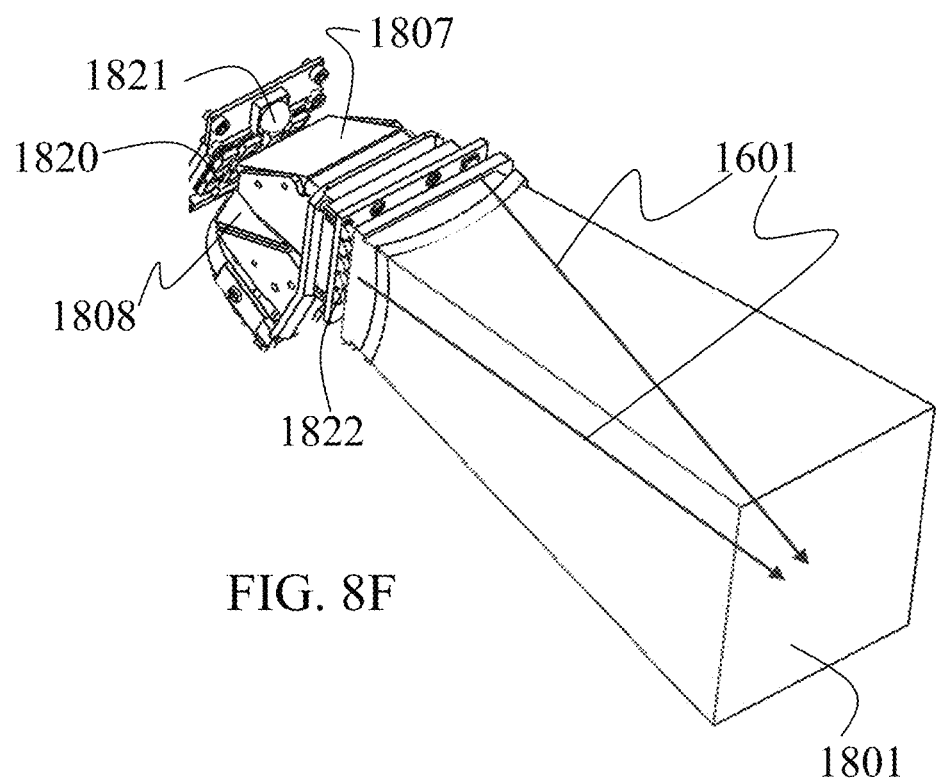
FIG. 8F presents a front view of the distal end of end of the optical system and the dark field illumination in the field of view (1601) of the embodiment illustrated in FIG. 8E.

Reference is now made to FIG. 8F, which presents a front view of the distal end of end of the optical system and the dark field illumination in the field of view. Shown are bright field LEDs 1820, dark field LEDs 1822, dichroic mirror 1807, beamsplitter 1808, and rays illustrating dark field (1601) radiation in the field of view.

In some embodiments of the invention, the image acquisition system acquires multi-spectral or video images. In some embodiments of the invention, the image acquisition system comprises an integrated laser ablation module for treatment of abnormal cells (e.g., cancerous cells in the uterine cervix).

Reference is made again to FIG. 8E, which presents a front view of the distal end of the optical system in an embodiment in which the system is used for bright field illumination and fluorescence measurements. Shown are bright field LEDs 1820 and 1821 for fluorescence, dichroic mirror 1807, beamsplitter 1808, and rays illustrating bright field (1603) and fluorescence (1602) radiation. Reference is now made to FIG. 8F, which presents a front view of the distal end of end of the optical system and the dark field illumination in the field of view. Also shown are bright field LEDs 1820 and 1821 for fluorescence, dark field LEDs 1822, dichroic mirror 1808, beamsplitter 1808, and rays illustrating dark field (1601) radiation in the field of view, bright field (1603), and fluorescence (1602) radiation.

In some embodiments of the invention, the image acquisition system acquires multi-spectral or video images. In some embodiments of the invention, the image acquisition system comprises an integrated laser ablation module for treatment of abnormal cells (e.g., cancerous cells in the uterine cervix).

In some embodiments, the optical design comprises at least one motor perpendicular to the optical system axis moving at least one optical component in two or more stages.

Some embodiments of the system herein disclosed in which it comprises a sliding mechanism are illustrated in FIGS. 8A-8F. In contrast to embodiments such as those shown in FIGS. 6A and 6B, which have a fixed magnification, the embodiments shown in FIGS. 8A-8F, provide for both variable working distance and variable magnification.

Reference is now made to FIG. 8A, which shows an isometric view of one embodiment of an optical train that comprises a sliding mechanism. In the embodiment shown in the figure, the optical train is housed inside of a disposable speculum. In the embodiment illustrated, four lens groups (some of which comprise a single lens) are mounted in mounts 3010, 3020, 3030, 3040 and 3050. The mounts are slidably mounted to track 3000 which is attached to the speculum. The track allows linear motion of the optic elements while keeping them aligned. Cogwheel 3031 is used to control the diameter of the aperture. In the embodiment shown, each of lens mounts 3020, 3030 and 3040 is slidably mounted to track 3000. In preferred embodiments of the system, each lens group can be moved independently of each of the others. In some embodiments of the system, the motion of the lens groups is actuated manually via mechanical connections running from the lens mounts to a point external to the housing (speculum, laparoscope, etc.) In other embodiments of the system, the motion of the lens groups is actuated by the motor or motors mentioned above, each of which is in mechanical connection with the lens mount or mounts that it controls.

There are two possible options for focusing:

Option 1: A fixed lens mechanical design that requires an optimal location positioning procedure. It is the physician who guides the disposable optical speculum with the camera head installed in front of the examined area (e.g., uterine cervix) and activates a fine tuning positioning process. In the optimal location positioning procedure, the image analysis and control unit continuously grabs images and produces focus results, which recommend to the physician to make final positioning corrections (see FIGS. 1A-1B).

Option 2: When using a non-fixed lens mechanical design, an automatic focus mechanism sets an optimal location of the lens. It is the physician who guides the disposable optical speculum with the camera head installed in front of the examined area (e.g., uterine cervix) and activates a fine tuning focus positioning process. In the optimal location positioning procedure, the image analysis and control unit continuously grabs images and produces the best focus results (see FIGS. 8A-8F).

In order to reach depth perception, there are three main features in this system.

1) The system has the option for a large depth of field.

2) Using the contiguous zoom feature, the system can receive a sequence of different images of the same (X,Y) position at different focal planes. In this method, good perception of the inspected object depth can be attained.

3) The system applies dark field illumination in different angles using an external illumination source element. As a non-limiting example, the system may be designed to divide and control the illumination source (e.g., two sections). By use of one section of the source in the first image and a second section of the source in the second image the system may provide depth perception of the inspected object.

High resolution over the whole field is assured in order to insure detection of all cancerous cells in one image.

Using these three methods the system can identify, for example, the thickness and surface topology of a tumor cell.

Figure 9:
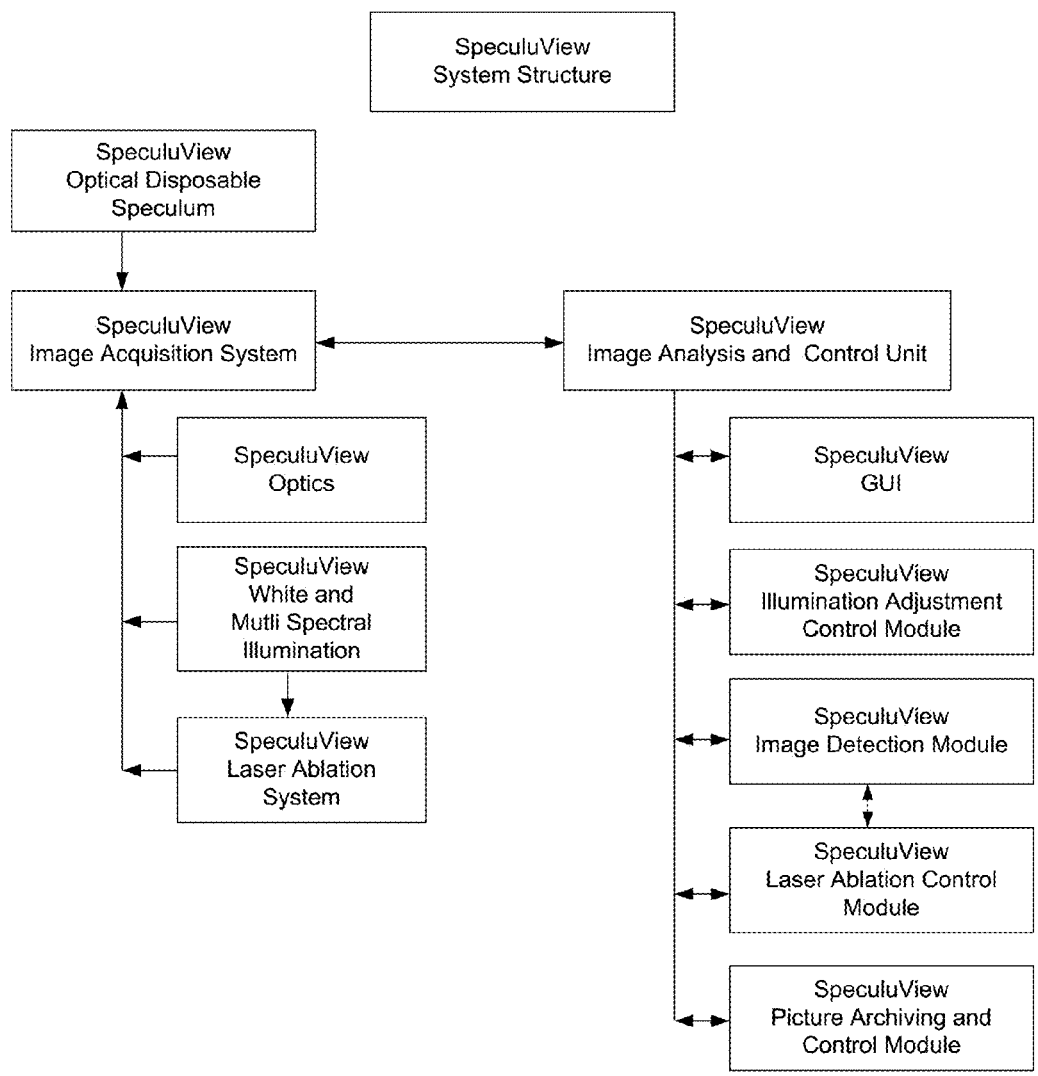
FIG. 9 presents the schematic structure of the system herein disclosed.

Reference is now made to FIG. 9, which shows a schematic structure of the SpeculuView system: Disposable optical speculum, Image Acquisition System modules, and Image Analysis and Control Unit modules.

Figure 10:
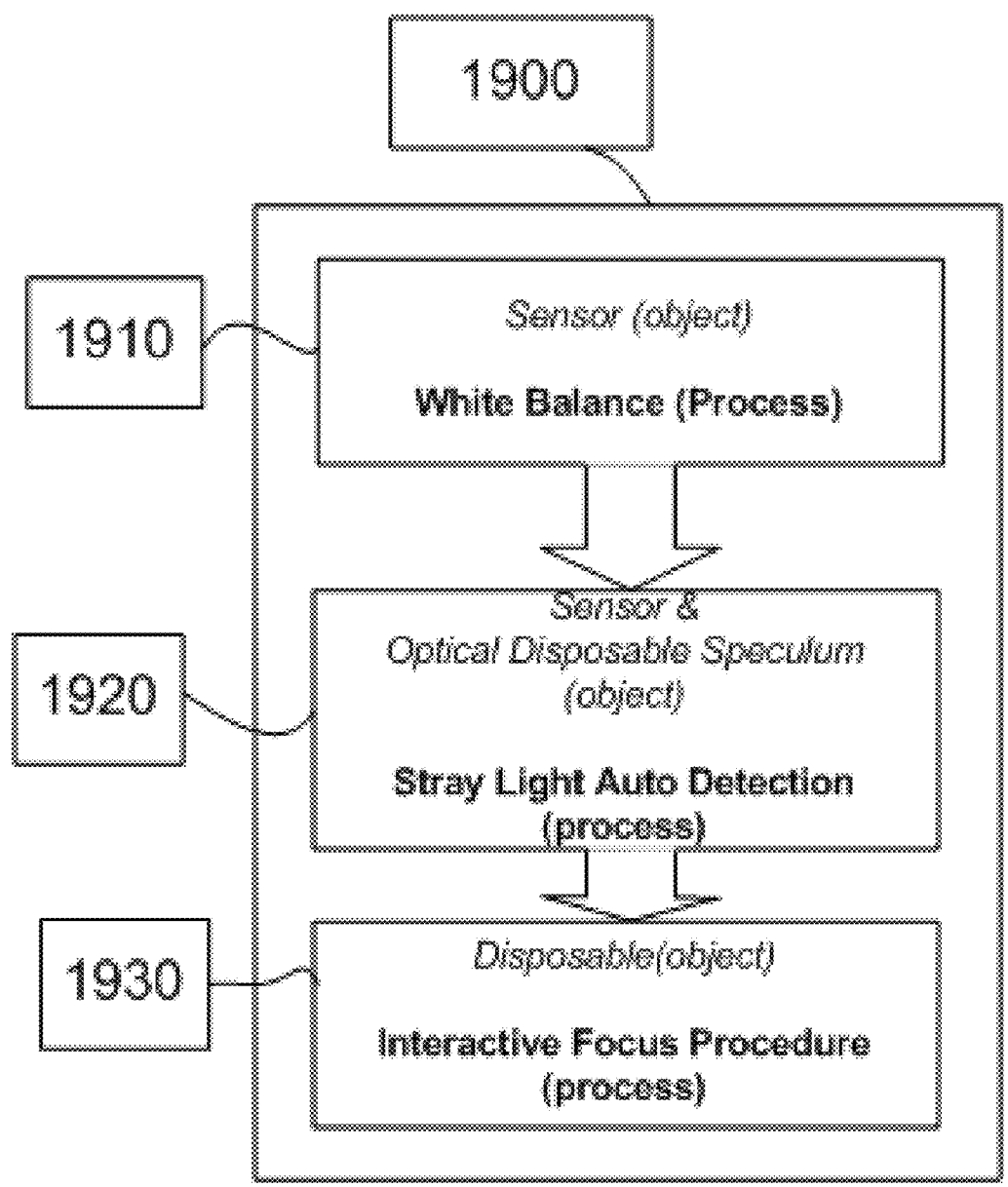
FIG. 10 illustrates the software initialization of the system herein disclosed.

Reference is now made to FIG. 10, which illustrates the software initialization flow (1900) in one preferred embodiment of the system herein disclosed. The software initialization module involves activation of the illumination source in the working limits within the dynamic range of the system, and recognition of stray light that indicates that the disposable optical speculum is not properly mounted.

In the embodiment shown in FIG. 10, the initialization routine for the image acquisition system illustrated in FIG. 10 begins with a self-calibration procedure (1910): the required amplification of the input signal needed to provide the best image for analysis is determined, and other steps of calibration of the image acquisition such as correction of the white balance to prevent acquisition of images with unrealistic color or gray levels are performed. A step (1920) of improper assembly detection is then performed. In this step, the image analysis and control unit verifies that the disposable optical speculum has been assembled and secured correctly. A manual interactive focusing procedure (1930) is them performed as needed.

Figure 11:
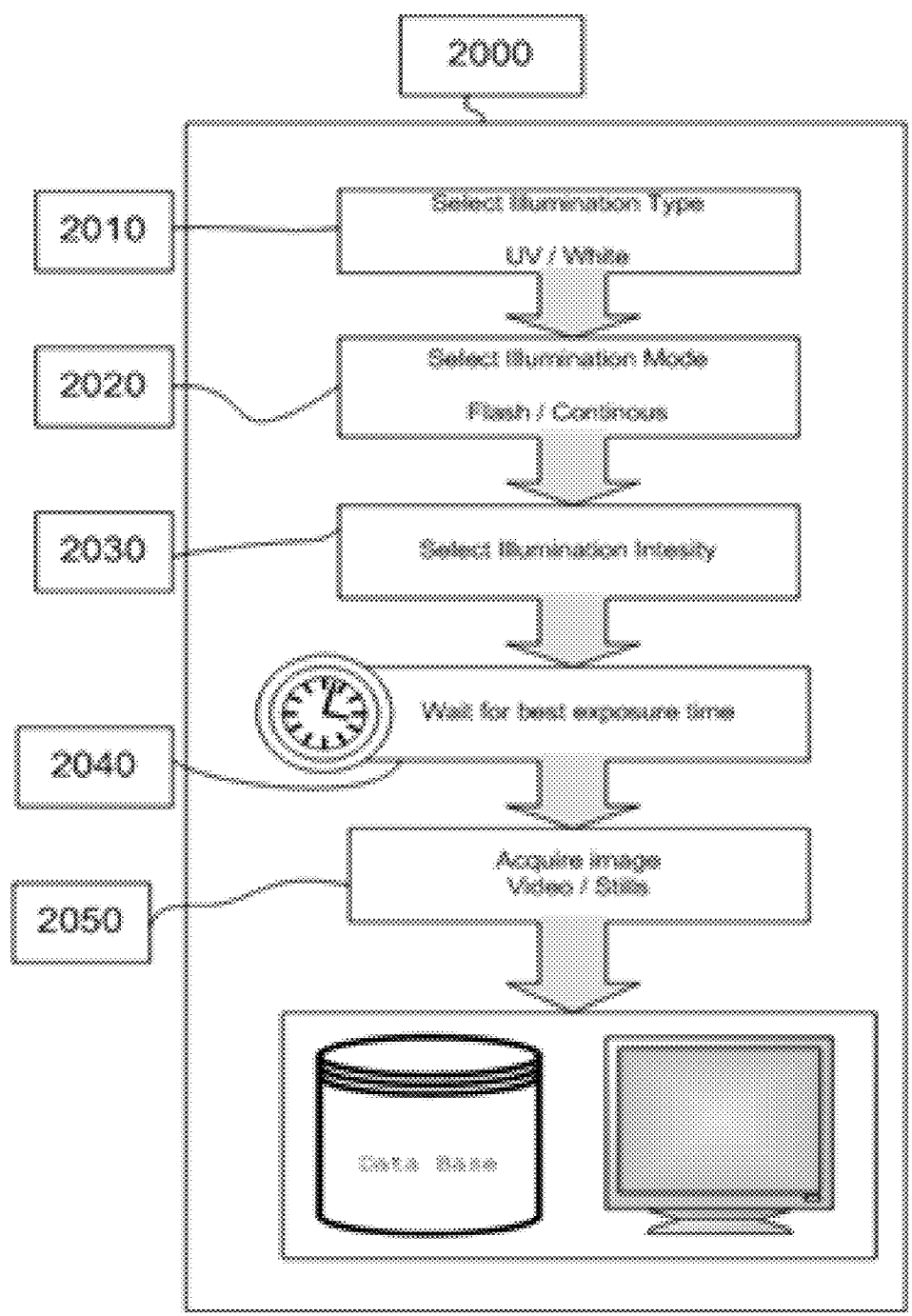
FIG. 11 illustrates an image capture algorithm process flow.

Reference is now made to FIG. 11, which illustrates image capture algorithm process flow 2000. A light source type (e.g. UV and/or white light) for image acquisition is selected (2010); the light mode (continuous or flash) is chosen for optimal detection (2020); the optimal illumination amplification (i.e. the illumination amplification that yields the optimal image acquisition) is selected (2030); the optimal illumination time is determined (2040); and an image is acquired and analyzed (2050) to determine whether any changes are needed for optimal image acquisition. If it is determined that changes are needed for optimal image acquisition, the image capture algorithm is reinitiated.

Figure 12:
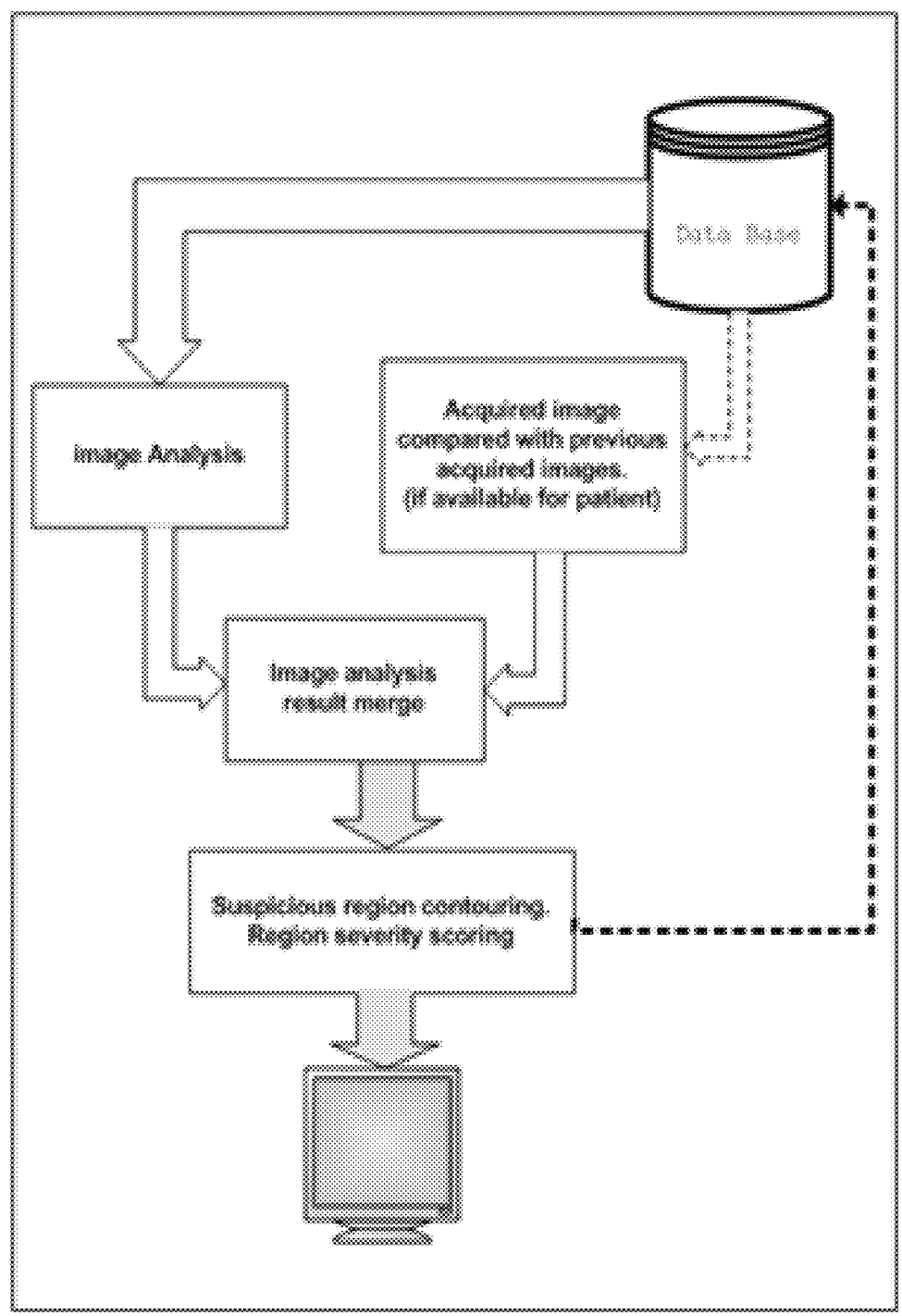
FIG. 12 illustrates the process of image analysis, display of suspicious areas by contours and the sensing algorithm.

Reference is now made to FIG. 12, which illustrates the process of image analysis, display of suspicious areas by contours and the scoring algorithm.

Figure 13:
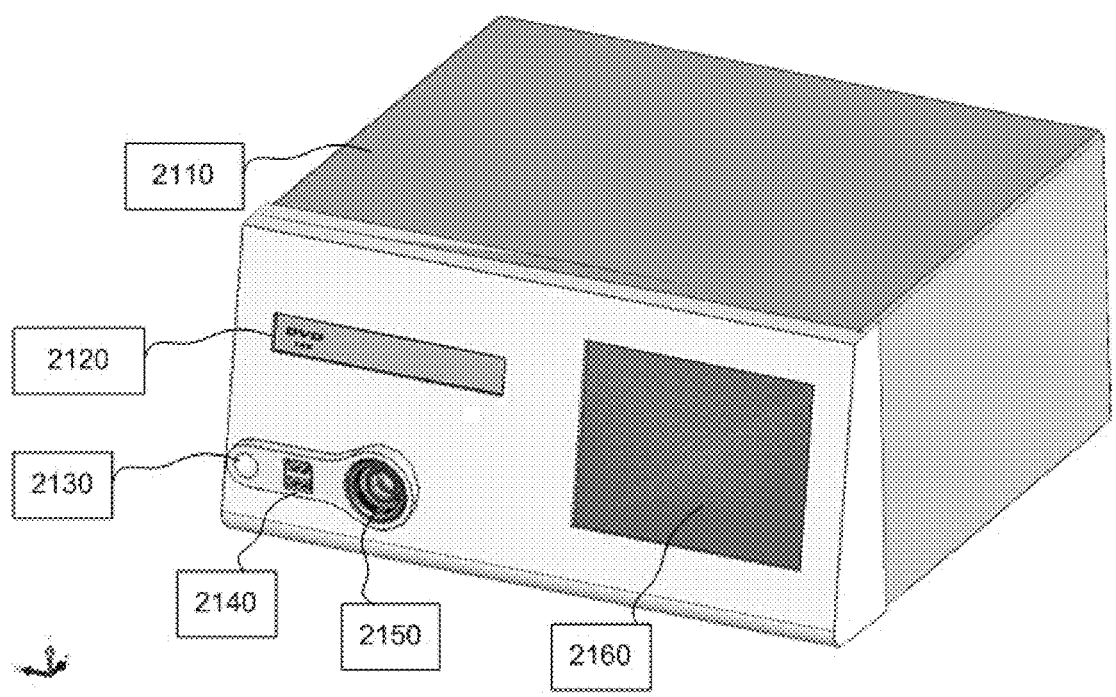
FIG. 13 illustrates one embodiment of an image analysis and control unit.

Reference is now made to FIG. 13, which illustrates an image acquisition system that is connected to the image analysis and control unit in preferred embodiments of the invention. The image analysis and control unit is a software package which may be implemented on special design hardware or a standard PC with custom hardware. The control and analysis system is provided in box 2110, and contains an optical read-write drive 2120 (non-limiting examples of suitable drives include DVD-RW and Blu-Ray-RW drives). Power to the control and analysis system is controlled by on/off operating button 2130. The camera head is connected to the analysis and control unit via a peripheral data connection 2140; the data connection may be of any suitable type known in the art such as USB. Also shown in the figure are image acquisition cable connector 2150 and the visual display 2160; in preferred embodiments of the invention, the visual display comprises an LCD touch screen.

The image analysis and control unit automatically adjusts the intensity of each illumination mode independently (i.e., white (bright field and or dark field illumination), multi-spectral illumination (e.g. UV and or IR)).

Data acquired from the examined area (e.g., uterine cervix) by the image acquisition system is analyzed by the image analysis and control unit which provides tissue diagnosis. In case there are abnormal cells, the image analysis and control unit identifies the suspicious regions which should be treated (e.g., by using a cell ablation system).

The disposable optical speculum may be coupled with a unique RFID (Radio Frequency Identification) tag. By assigning to each speculum a unique serial/lot number, the image analysis and control unit will assure the use of a brand new disposable optical speculum for each patient and for each examination. The tag number associated with the disposable optical speculum will be specified in the patient's examination file.

The image analysis and control unit is able to analyze white and/or multi spectral images taken under the use of reflectance and auto-fluorescence reagents (i.e., contrast agents).

The image analysis and control unit is based on an open, modular, and feature-based architecture. Analysis methods are designed for use with one or more imaging sensors, white and/or multi spectral illumination types.

In some preferred embodiments of the invention, the image analysis and control unit provides methods based on unique algorithms for accurate removal of abnormal cells (e.g., by identifying their margins). In some preferred embodiments of the system, the image analysis and control unit comprises an algorithm to create a map of contours, namely the borders between healthy and abnormal cells. In some embodiments of the invention, the image analysis and control unit uses Picture Archiving and Control System (PACS) methods for image archiving and management.

Reflectance and/or fluorescence images are acquired from the abnormal cells. Optionally, the reflectance and/or fluorescence images may be acquired using a short pulse of light to illuminate the tissue being examined. Various reflectance and fluorescence images may be acquired under the same, or different, configurations of illumination.

Abnormal cells may be destroyed by ablation. The ablation procedure is operated either automatically, or by manual control of the set of adjustable mirrors to focus on candidate abnormal cells. Upon completion of destruction by ablation, additional reflectance or fluorescence images may be acquired to verify the completion of the procedure.

In typical embodiments of the invention, the laser ablation system comprises an imaging sensor, a flexible/solid optical fiber, a laser system, a set of mirrors near the laser head and near the beam splitter which is located near the tip of the fiber, and an optical system that locally images the tested area. In some preferred embodiments of the invention, a long pass filter is located between the lens and the fibers in order to subtract the Violet/UV light from the image for fluorescence.

In some embodiments of the invention, the laser ablation system is located in the area of the imaging sensors 1315.

In typical embodiments of the invention that incorporate a laser ablation system, the laser ablation is performed by passing a pulsed laser beam through collimating optics, a set of mirrors, a fiber bundle, another mirror, a beam splitter and second focusing optics. There are two optional places to use a motorized adjustable set of mirrors. In the case where a straight solid fiber bundle is used, the laser beam location can be adjusted using the mirrors near the laser, otherwise the adjustable steering mirror may be positioned in front of the beam splitter near the edge of the fiber bundle and its tilted angles controlled remotely. This adjustable set of mirrors receives a set of angles/travels as an output from the image analysis report or a set of points from the physician manually to manipulate the orientation laser beam to selectively impinge on desired locations of malignant tissue to be destroyed.

Overcoming deficiencies of prior art colposcope systems, the system according to the present invention provides:

a disposable optical speculum with a working channel for the physician;

a small camera with multi spectral internal illumination systems:

bright field LEDs (through the lens) illumination;

dark field LEDs illumination with a specific illumination angle;

an internal UV illumination ("through the lens illumination") for abnormal cell detection by fluorescence or auto fluorescence;

an internal IR illumination ("through the lens illumination");

an opportunity to examine with sufficient resolution fine objects at a short distance with maximum patient protection; and, optional in situ laser ablation of abnormal cells (e.g., cancerous cells).

The disposable optical speculum may provide a working channel, and an adjustable locking mechanism for lower and upper speculum blades.

The working channel may be used for obtaining a Pap-Smear specimen, and passing working tools (e.g., biopsy tools).

The invention separately provides a disposable optical speculum which is a part of the whole optical design and is assembled on the image acquisition system, thus providing a safe cross contamination protection for the examined patient.

The invention provides a high resolution imaging system which comprises one or more imaging sensors, thus providing high dynamic range image. The importance of such information is that it can be used for computer calculation since such an image with high dynamic range is hard to display or print.

The invention separately may provide a system and methods including a detection algorithm for abnormal cell screening.

The invention may provide a special abnormal cell detection algorithm designed specifically for the uterine cervix.

The optical system may comprise a design of an optical zoom lens system along the optical axis, or a discrete zoom design (e.g., slider design).

The image acquisition system is an electro optical element which functions as an integrated system for multi spectral imaging and treatment. The image acquisition system is locked to the disposable optical speculum with a releasable secured mechanical lock.

This invention provides a system and methods for high resolution imaging of the examined area (e.g., uterine cervix). The system provides image analysis for tissue abnormalities.

The invention may be used as an image analysis for tissue abnormalities such as cervical intraepithelial neoplasia (CIN) or invasive cancer.

The system control and analysis unit provides a real time image or live video that is acquired from the examined area (e.g. the uterine cervix). It provides tissue diagnosis and it may provide the ability to ablate, in an accurate manner, the abnormal cancerous cells. Images or live video and analysis results are displayed both to the physician and patient.

The imaging acquisition system acquires color and/or monochrome images. The acquired data of the examined area is analyzed by the image analysis and control unit. The image and analysis control unit outputs a graphical representation of suspicious regions and classification of the detected tissue.

The imaging acquisition system may acquire color and/or monochrome images from the uterine cervix.

There are two main image capture modes. Manual mode requires the physician to control the illumination parameters before the image is acquired and delivered for final analysis. Automatic mode does not require any intervention of the physician with respect to the illumination configuration. As described in detail above, the algorithm for setting the optimal image capture parameters continuously grabs images while changing the values of illumination type, mode, intensity and exposure time in order to produce an optimal image for analysis.

A numerical analysis for autofluorescence imaging for pathological tissue detects a cancerous area in a given image. The numerical analysis for auto fluorescence imaging includes a pathological tissue algorithm that uses the special characteristics of the reflected ultraviolet light source. The numerical analysis for autofluorescence imaging for pathological tissue detects and renders suspicious regions in a given image, and generates a pathological lesion scoring for the region.

As mentioned above, the present invention can also be utilized in hysteroscopy procedures. In such procedures the image acquisition system can be utilized to perform direct imaging, diagnosing and treatment within the uterus. In such embodiments, the system is assembled on and mechanically secured to a hysteroscope.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A speculum comprising:
a camera housing having a distal end and a proximal end;
two rigid blade members mounted to the camera housing and having a closed configuration and at least one open configuration, including an upper blade member pivotally and slidably mounted to the distal end of the camera housing and a lower blade member mounted to the camera housing; and
a lens integrally formed with the lower blade member forward of the camera housing, the speculum and integral lens removably attached to an image acquisition system disposed within the camera housing such that the speculum and lens are disposable.

2. The speculum of claim 1, wherein the upper blade member is capable of moving independently of the lower blade member.

3. The speculum of claim 1, wherein the lower blade member comprises at least one fluid transporting member connected to a drain hole provided therein for transporting liquid and gas to or from a location proximal to the camera housing, and at least one extraction tube secured to the drain hole for transporting fluid, the extraction tube comprising a proximal end and a distal end, the proximal end fluidly connectable to a fluid or suction source located proximal to the camera housing.

4. The speculum of claim 3, wherein the extraction tube passes through the camera housing.

5. The speculum of claim 3, wherein the extraction tube passes outside of the camera housing.

6. The speculum of claim 3, wherein the fluid transporting member includes at least one channel, at least one tube, or a combination thereof.

7. The speculum of claim 3, wherein the fluid transporting member extends to an end of the lower blade member.

8. The speculum of claim 3, wherein the fluid transporting member terminates at a location within a volume encompassed by the lower blade member.

9. The speculum of claim 3, further comprising at least a first extraction tube fluidly attachable to the fluid source and a second extraction tube fluidly connectable to the suction source, the first extraction tube adapted to transport fluid to the lower blade member, and the second extraction tube adapted to withdraw fluid from the lower blade member.

10. The speculum of claim 1, wherein the speculum is attached to the image acquisition system via attachments that are disabled after detaching the image acquisition system from the speculum.

11. The speculum of claim 1, wherein the lens includes an elastic layer for preventing stray light from entering the image acquisition system.

12. The speculum of claim 1, wherein the lens includes a linear cylindrical collimating lens for a dark field LED source in the image acquisition system which leaves a working channel for treatment.

* * * * *